(12) United States Patent
Michelson

(10) Patent No.: US 7,033,394 B2
(45) Date of Patent: *Apr. 25, 2006

(54) INTERBODY SPINAL FUSION IMPLANTS WITH END CAP FOR LOCKING VERTEBRAL BODY PENETRATING MEMBERS

(75) Inventor: Gary K. Michelson, Venice, CA (US)

(73) Assignee: SDGI Holdings, Inc., Wilmington, DE (US)

( * ) Notice: Subject to any disclaimer, the term of this patent is extended or adjusted under 35 U.S.C. 154(b) by 87 days.

This patent is subject to a terminal disclaimer.

(21) Appl. No.: 10/444,216

(22) Filed: May 23, 2003

(65) Prior Publication Data

US 2003/0199983 A1  Oct. 23, 2003

Related U.S. Application Data

(60) Continuation of application No. 10/310,522, filed on Dec. 5, 2002, which is a division of application No. 09/565,392, filed on May 5, 2000, now Pat. No. 6,558,423.

(60) Provisional application No. 60/132,665, filed on May 5, 1999, provisional application No. 60/133,214, filed on May 7, 1999.

(51) Int. Cl.
 *A61F 2/44* (2006.01)
(52) U.S. Cl. .................................... 623/17.11
(58) Field of Classification Search .. 623/17.11–17.13, 623/17.16, FOR. 17
See application file for complete search history.

(56) References Cited

U.S. PATENT DOCUMENTS

| 3,426,364 A | 2/1969 | Lumb |
| 3,875,595 A | 4/1975 | Froning |
| 4,349,921 A | 9/1982 | Kuntz |
| 4,501,269 A | 2/1985 | Bagby |
| RE31,865 E | 4/1985 | Roux |

(Continued)

FOREIGN PATENT DOCUMENTS

DE    3 505 567 A1    5/1986

(Continued)

OTHER PUBLICATIONS

Crock, H.V.; Practice of Spinal Surgery; Springer-Verlag/Wien, New York (1983), pp. 74-85.

(Continued)

*Primary Examiner*—David H. Willse
(74) *Attorney, Agent, or Firm*—Martin & Ferraro, LLP

(57) ABSTRACT

An apparatus including an interbody spinal fusion implant having a leading end, a trailing end, and a length therebetween, and opposed upper and lower portions adapted to contact each of the adjacent vertebral bodies. Each of the upper and lower portions having at least one opening adapted to communicate with one each of the adjacent vertebral bodies and to communicate with one another to permit for the growth of bone from vertebral body to adjacent vertebral body through the implant. Each of the upper and lower portions has at least one screw hole passing therethrough proximate the trailing end. The apparatus further includes bone screws adapted for placement through the screw holes of the upper and lower portions and into each of the adjacent vertebral bodies adjacent the disc space to be fused and into which the implant is adapted to be positioned. At least one lock may be used to prevent the bone screws from backing out of the vertebral bodies and implant.

49 Claims, 22 Drawing Sheets

U.S. PATENT DOCUMENTS

| | | |
|---|---|---|
| 4,599,086 A | 7/1986 | Doty |
| 4,636,217 A | 1/1987 | Ogilvie et al. |
| 4,714,469 A | 12/1987 | Kenna |
| 4,743,256 A | 5/1988 | Brantigan |
| 4,759,769 A | 7/1988 | Hedman et al. |
| 4,820,305 A | 4/1989 | Harms et al. |
| 4,877,020 A | 10/1989 | Vich |
| 4,878,915 A | 11/1989 | Brantigan |
| 4,904,261 A | 2/1990 | Dove et al. |
| 4,955,908 A | 9/1990 | Frey et al. |
| 4,961,740 A | 10/1990 | Ray et al. |
| 5,015,247 A | 5/1991 | Michelson |
| 5,026,373 A | 6/1991 | Ray et al. |
| 5,055,104 A | 10/1991 | Ray |
| 5,258,031 A | 11/1993 | Salib et al. |
| 5,397,364 A | 3/1995 | Kozak et al. |
| 5,425,772 A | 6/1995 | Brantigan |
| 5,458,638 A | 10/1995 | Kuslich et al. |
| 5,489,307 A | 2/1996 | Kuslich et al. |
| 5,489,308 A | 2/1996 | Kuslich et al. |
| 5,571,109 A | 11/1996 | Bertagnoli |
| 5,593,409 A | 1/1997 | Michelson |
| 5,609,636 A | 3/1997 | Kohrs et al. |
| 5,645,598 A | 7/1997 | Brosnahan, III |
| 5,658,337 A | 8/1997 | Kohrs et al. |
| 5,669,909 A | 9/1997 | Zdeblick et al. |
| 5,683,463 A | 11/1997 | Godefroy et al. |
| 5,766,252 A | 6/1998 | Henry et al. |
| 5,776,196 A | 7/1998 | Matsuzaki et al. |
| 5,782,919 A | 7/1998 | Zdeblick et al. |
| D397,439 S | 8/1998 | Koros et al. |
| 5,800,547 A | 9/1998 | Schäfer et al. |
| 5,800,550 A | 9/1998 | Sertich |
| 5,814,084 A | 9/1998 | Grivas et al. |
| 5,861,041 A | 1/1999 | Tienboon |
| 5,888,223 A | 3/1999 | Bray, Jr. |
| 5,904,719 A | 5/1999 | Errico et al. |
| 6,033,438 A | 3/2000 | Bianchi et al. |
| 6,066,175 A | 5/2000 | Henderson et al. |
| 6,206,922 B1 | 3/2001 | Zdeblick et al. |

FOREIGN PATENT DOCUMENTS

| | | |
|---|---|---|
| EP | 0 179 695 A1 | 4/1986 |
| EP | 0 599 419 A2 | 6/1994 |
| EP | 0 637 440 B1 | 10/1997 |
| ES | 283078 | 5/1985 |
| FR | 2 727 003 | 5/1996 |
| WO | WO 94/26193 A1 * | 11/1994 |
| WO | 95/26164 | 10/1995 |

OTHER PUBLICATIONS

Bagby, G.W.; Arthrodesis by the Distraction-Compression Method Using a Stainless Steel Implant; Orthopedics, vol. II, No. 6, pp. 931-934 (Jun. 1987).

Laparoscopic Bone Dowel Surgical Technique; Brochure of Sofamor Danek (1995).

Brochure of University of Florida Tissue Bank; MD-I and MD-II Custom Machine Cortical Dowels; (*Circa* 1996).

Brochure of University of Florida Tissue Bank; MD-III Threaded Cortical Dowel; (*Circa* 1996).

Glazer, P.A., et al.; Biomechanical Analysis of Multilevel Fixation Methods in the Lumbar Spine; Spine, vol. 22, No. 2, pp. 171-182 (1997).

Ray, C.D.; Spinal Interbody Fusions: A Review, Featuring New Generation Techniques; Neurosurgery Quarterly, 7(2): 135-156 (1997).

A picture of a Medtronic, Sofamor Danek Display; titled "Evolving With Your Needs" (Apr. 6, 2000).

* cited by examiner

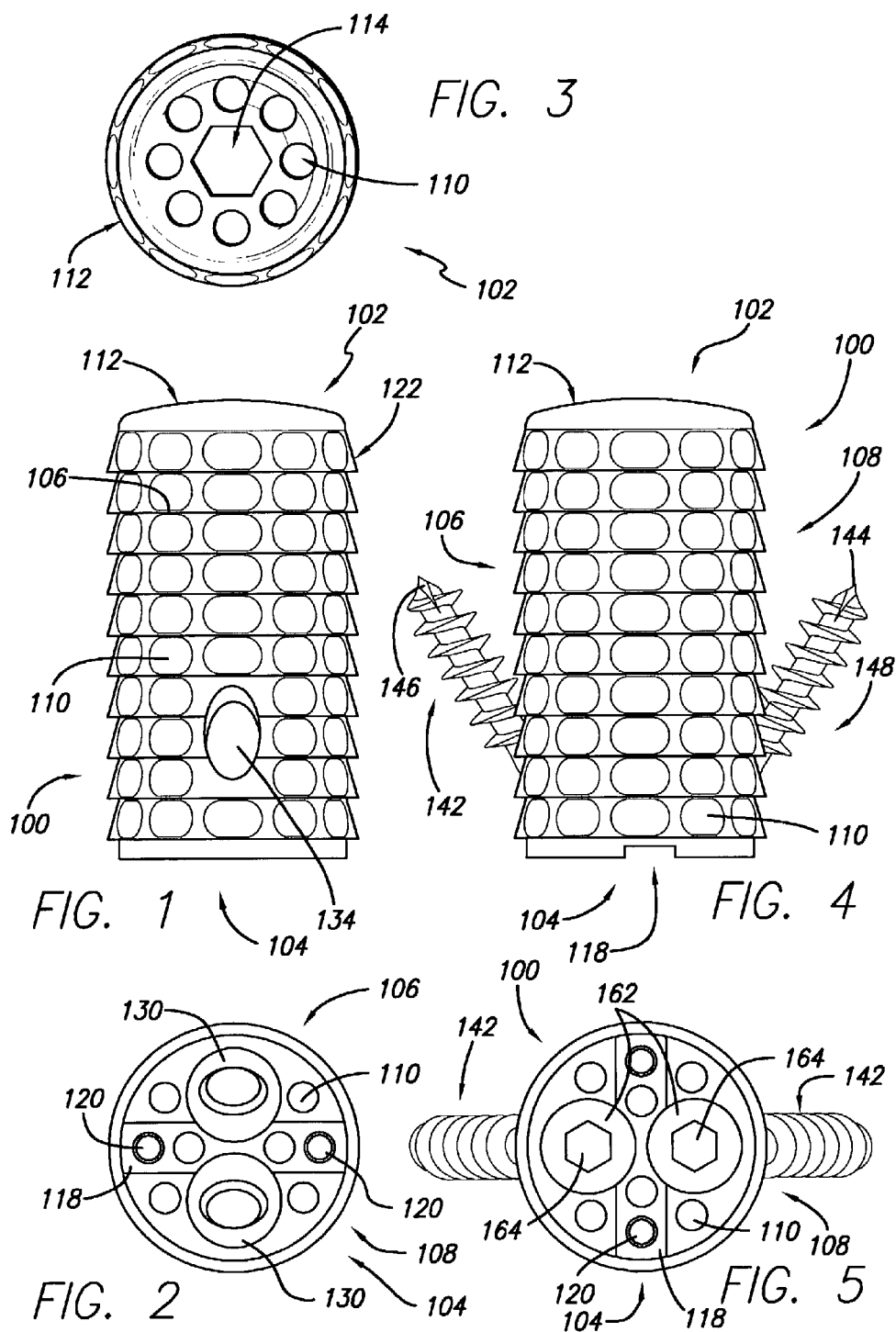

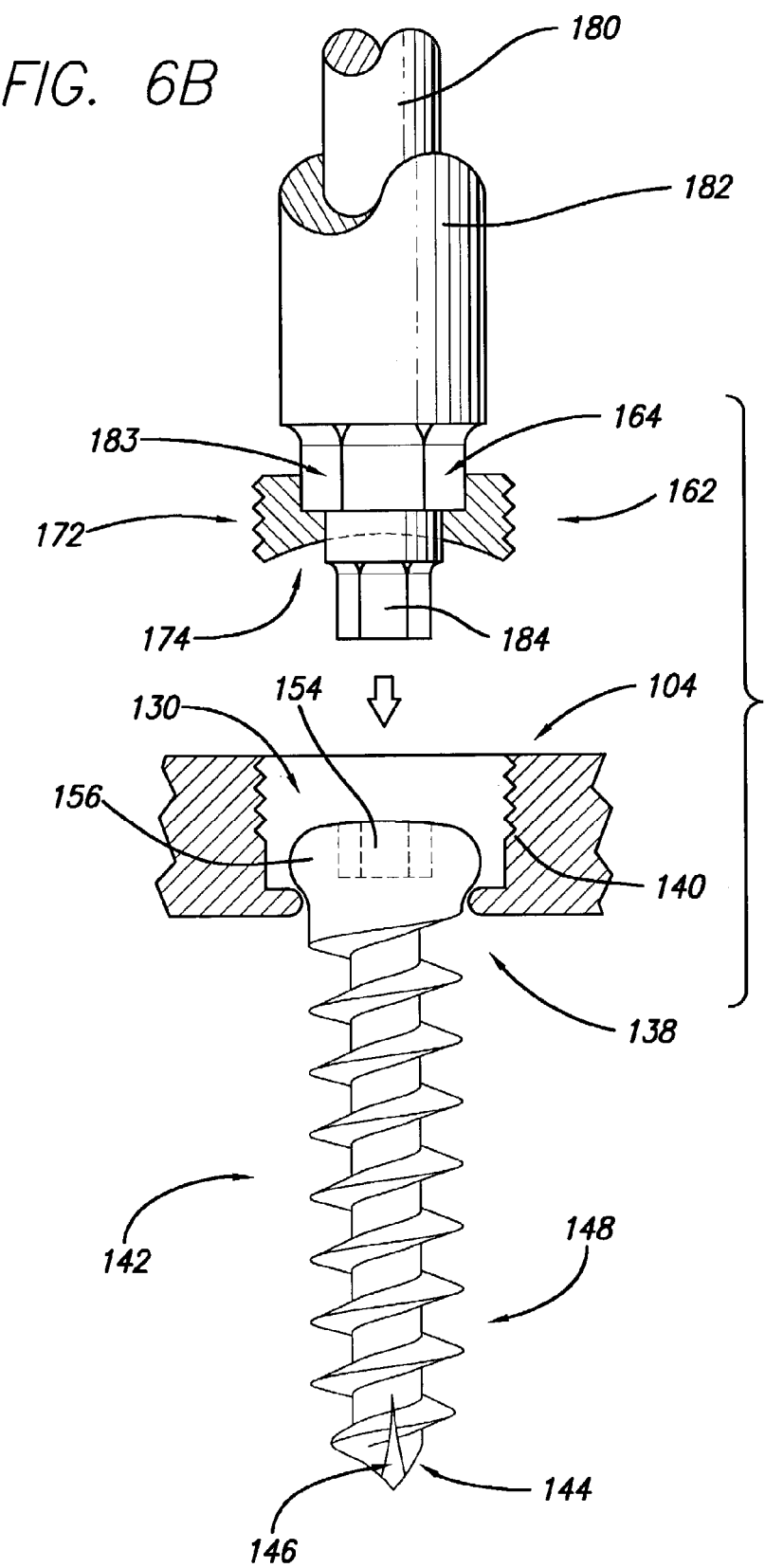

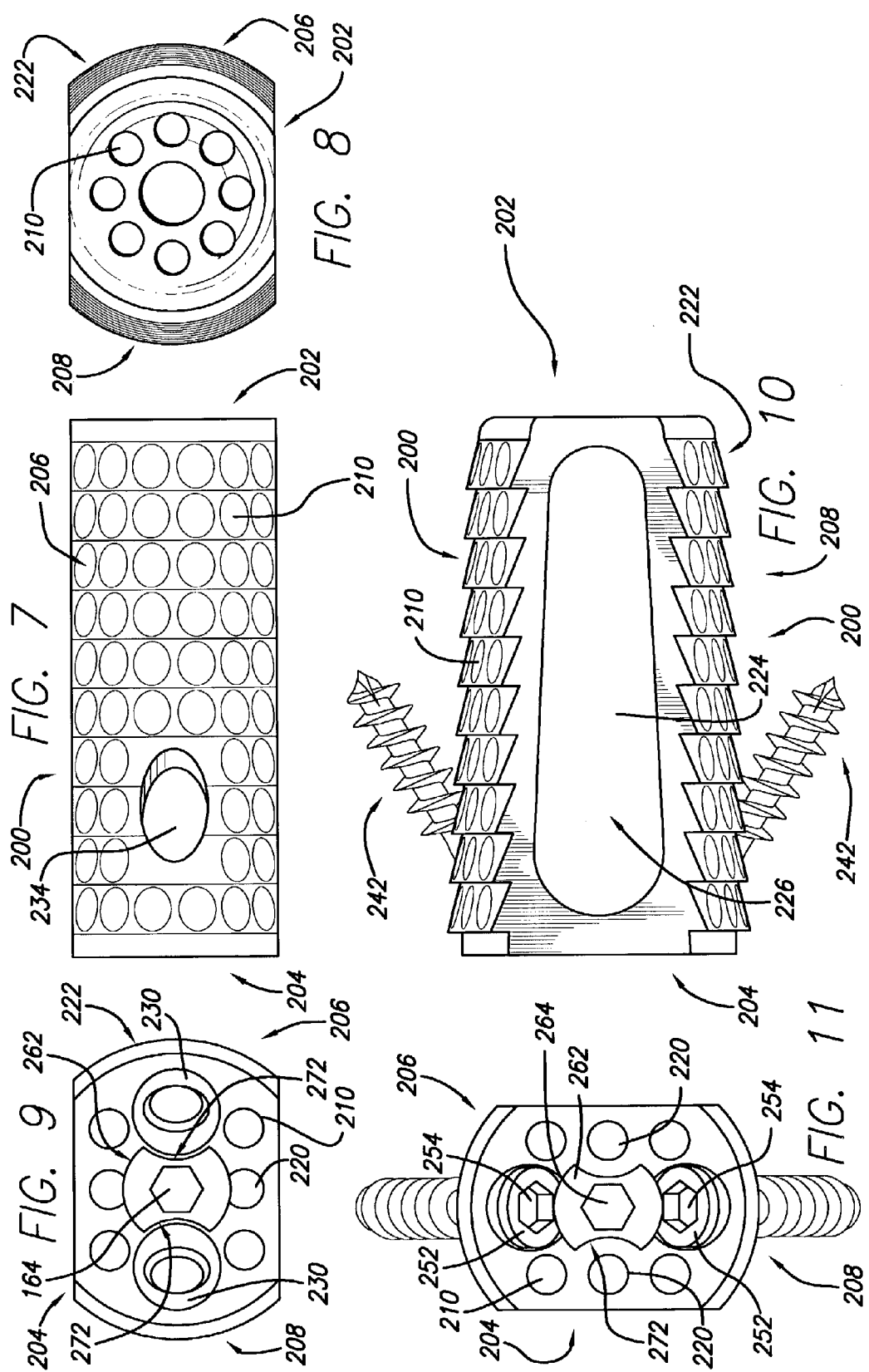

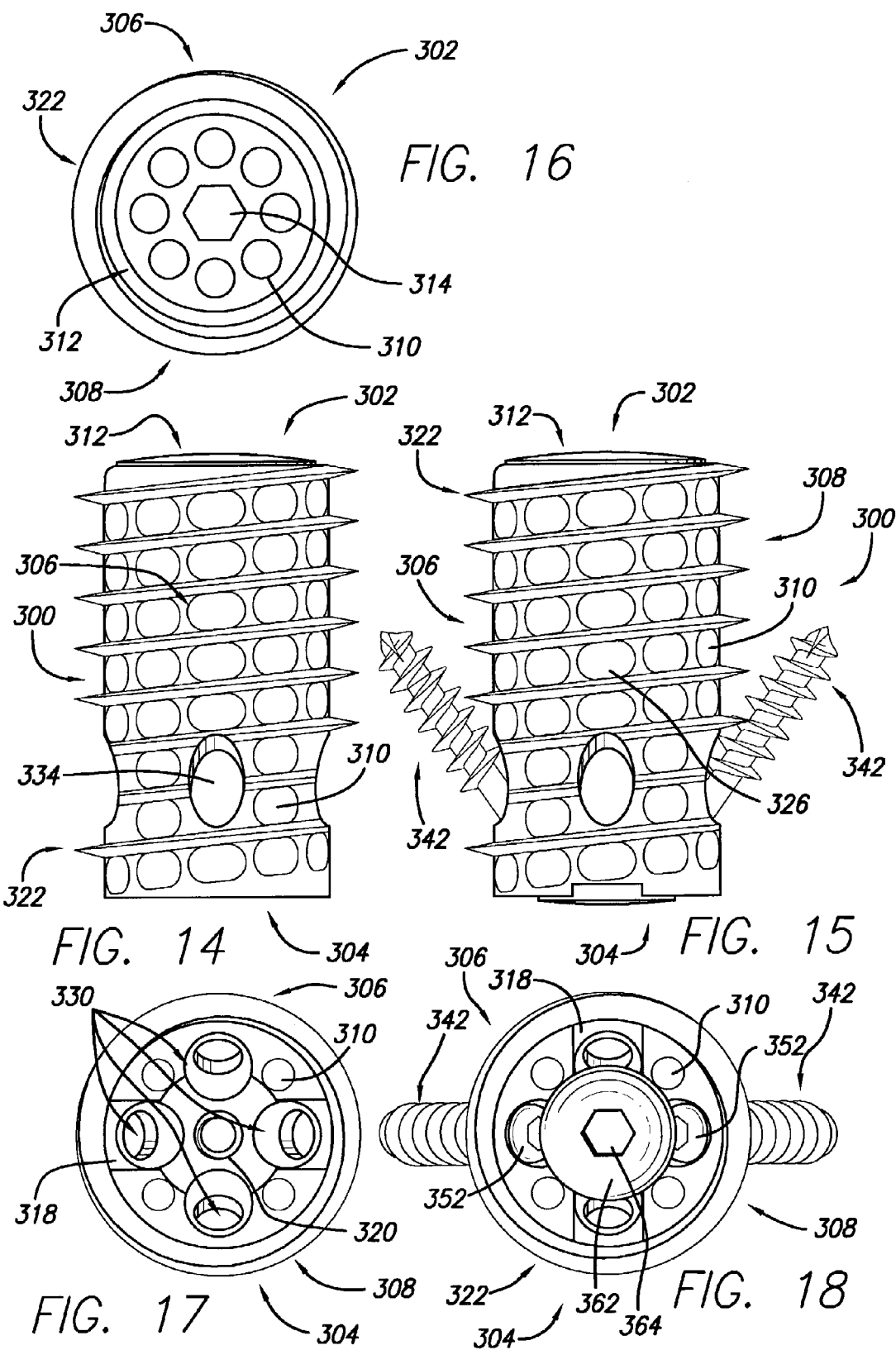

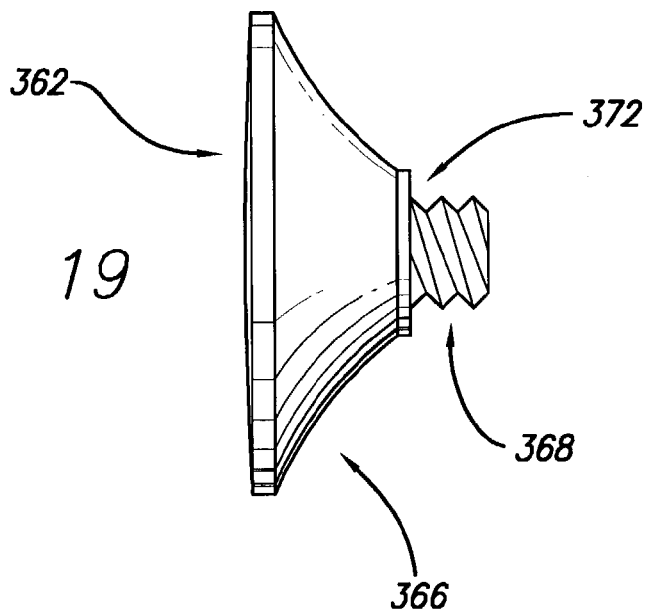
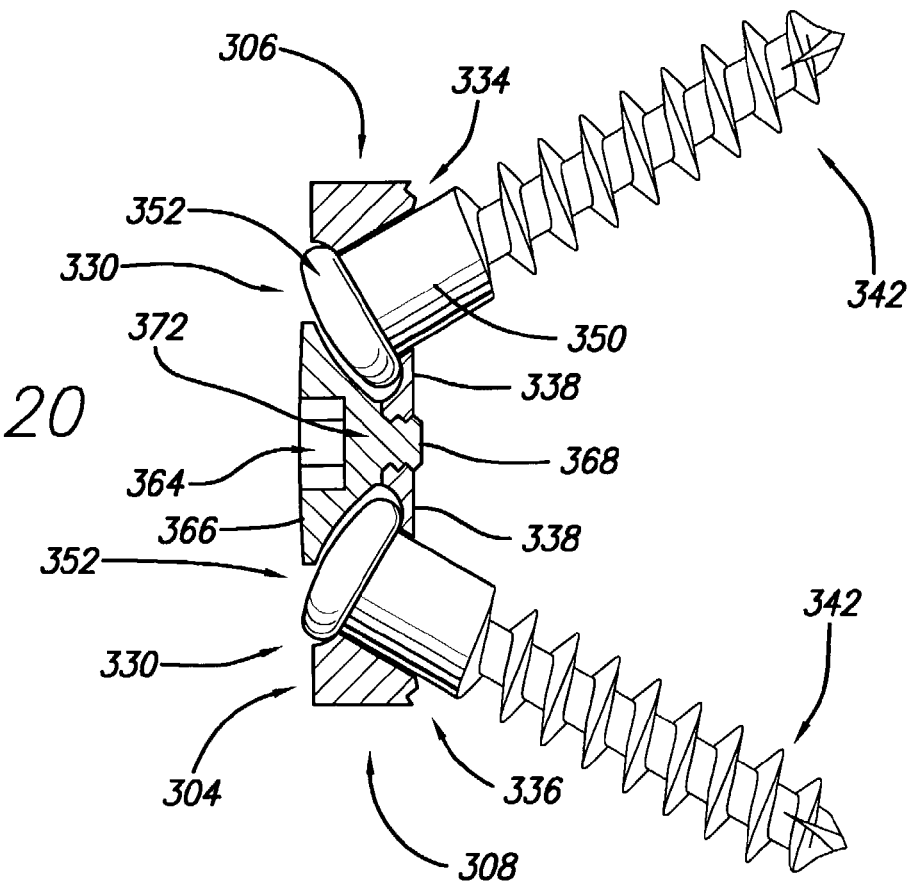

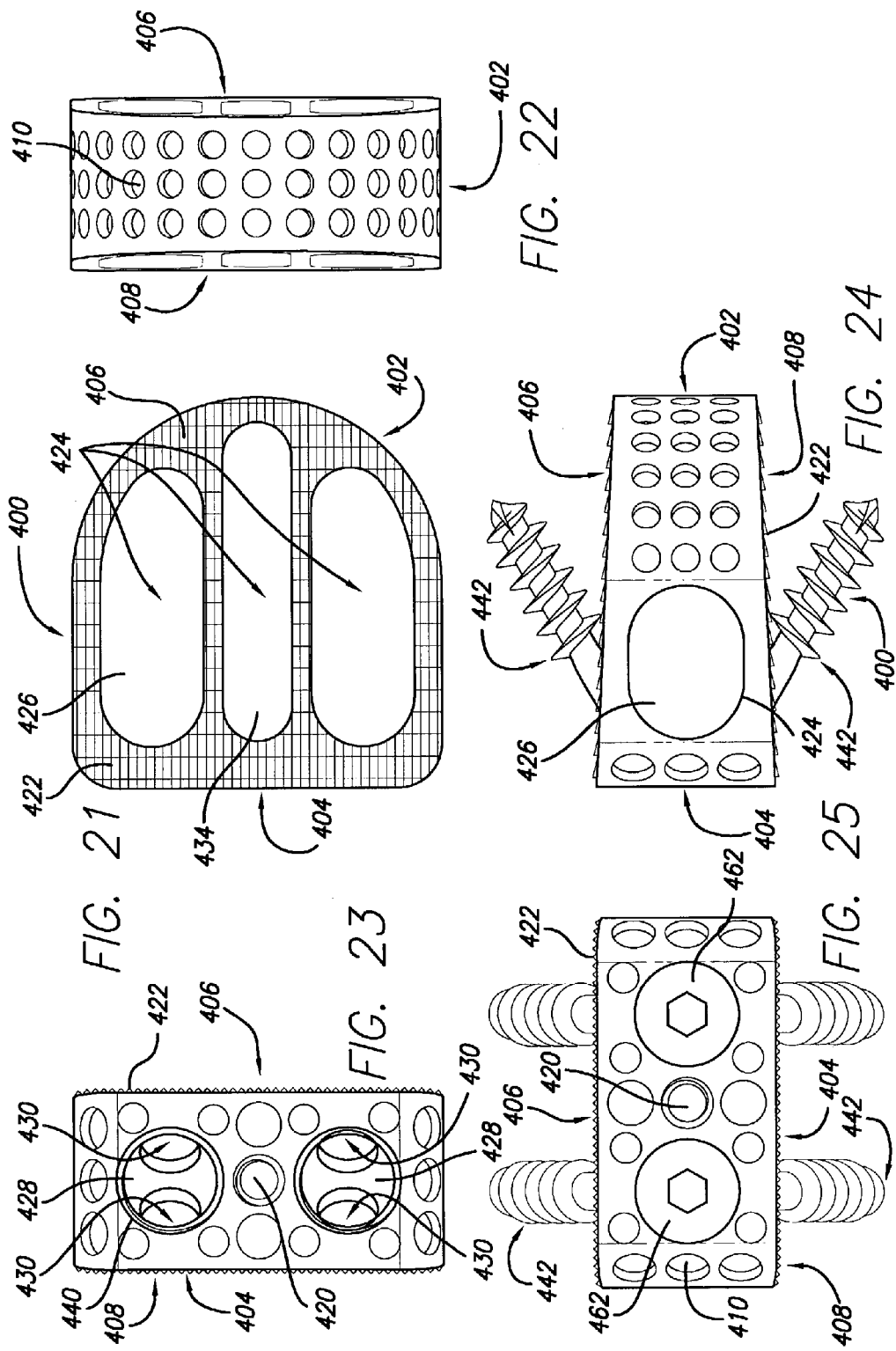

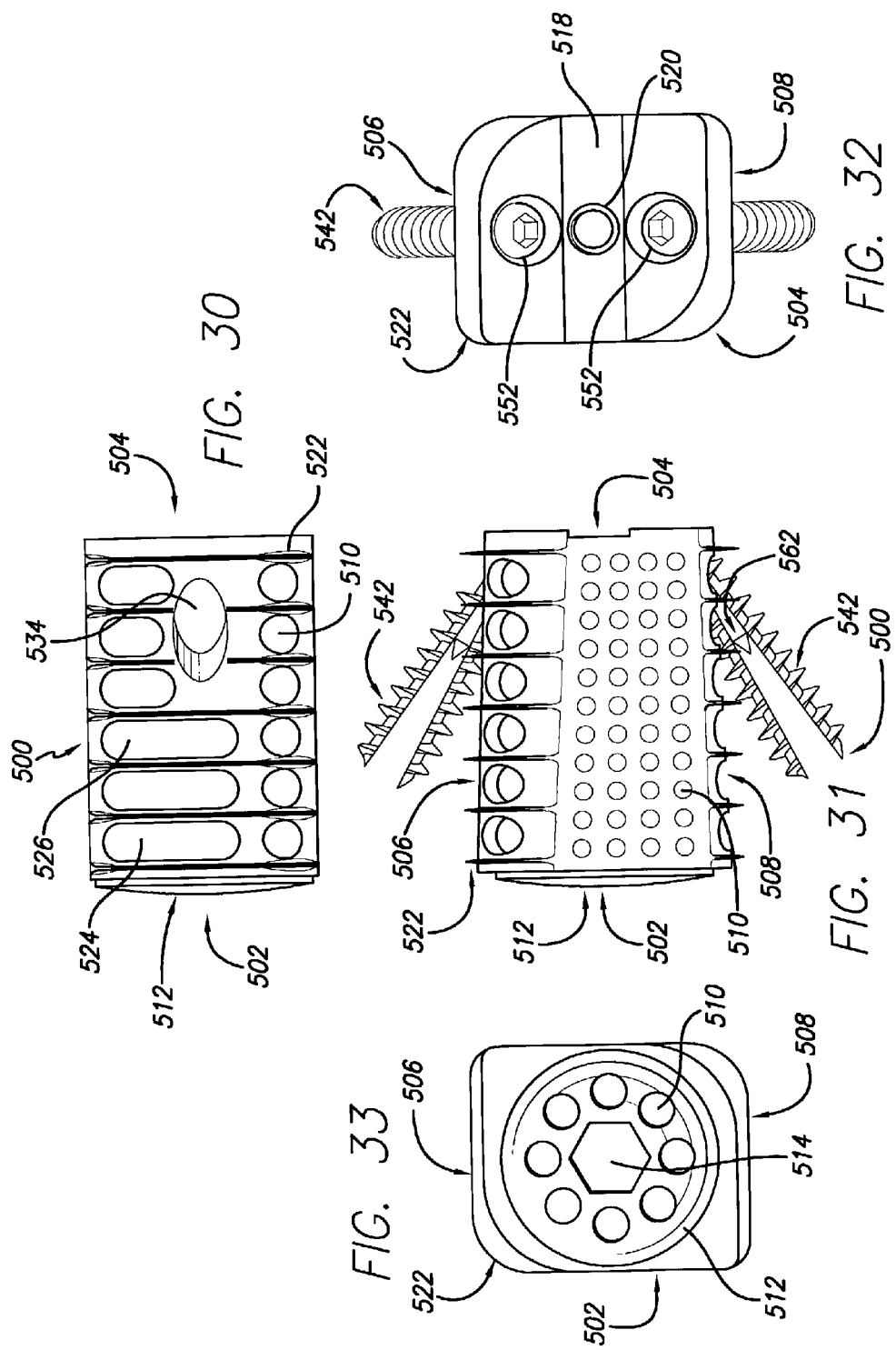

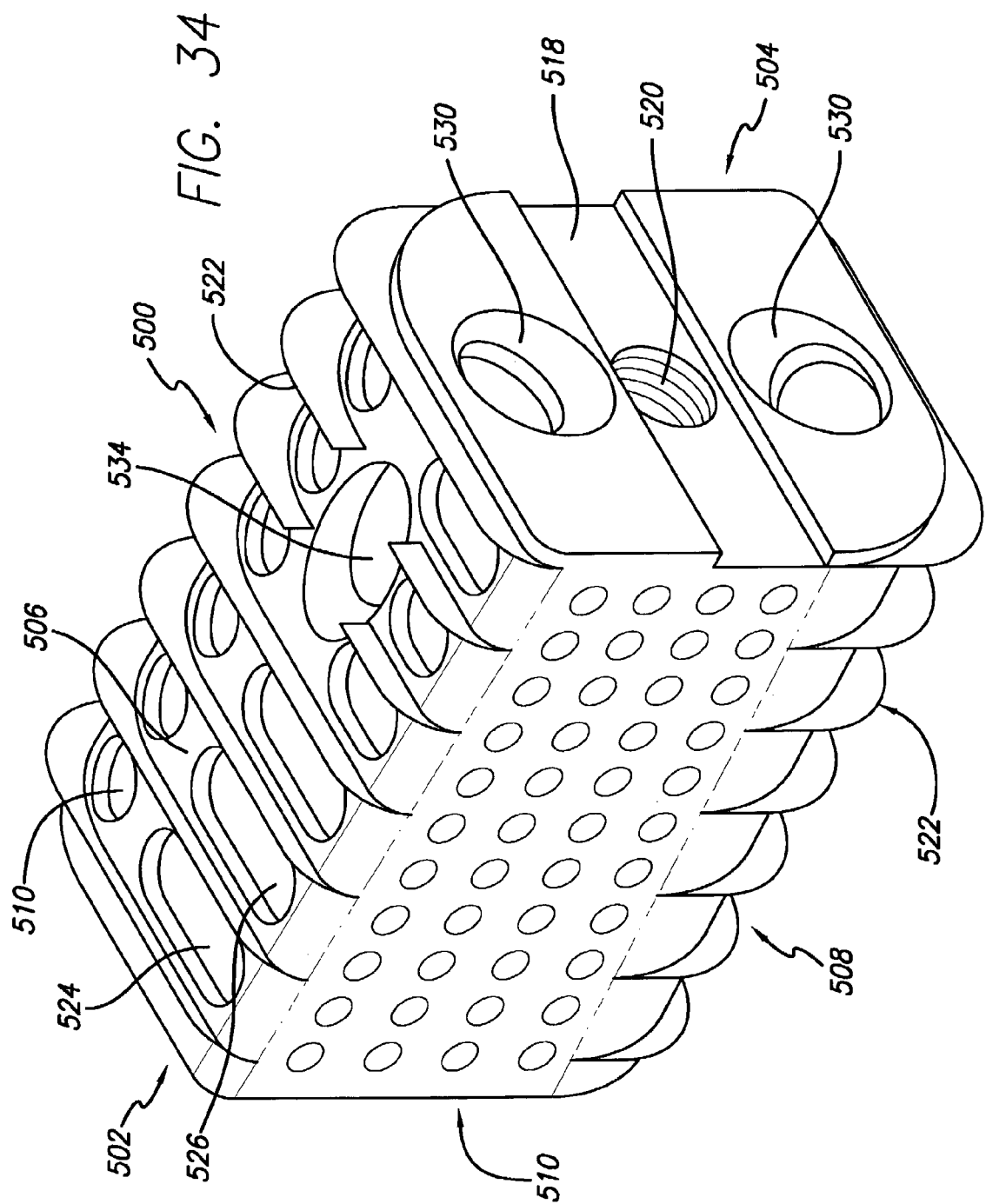

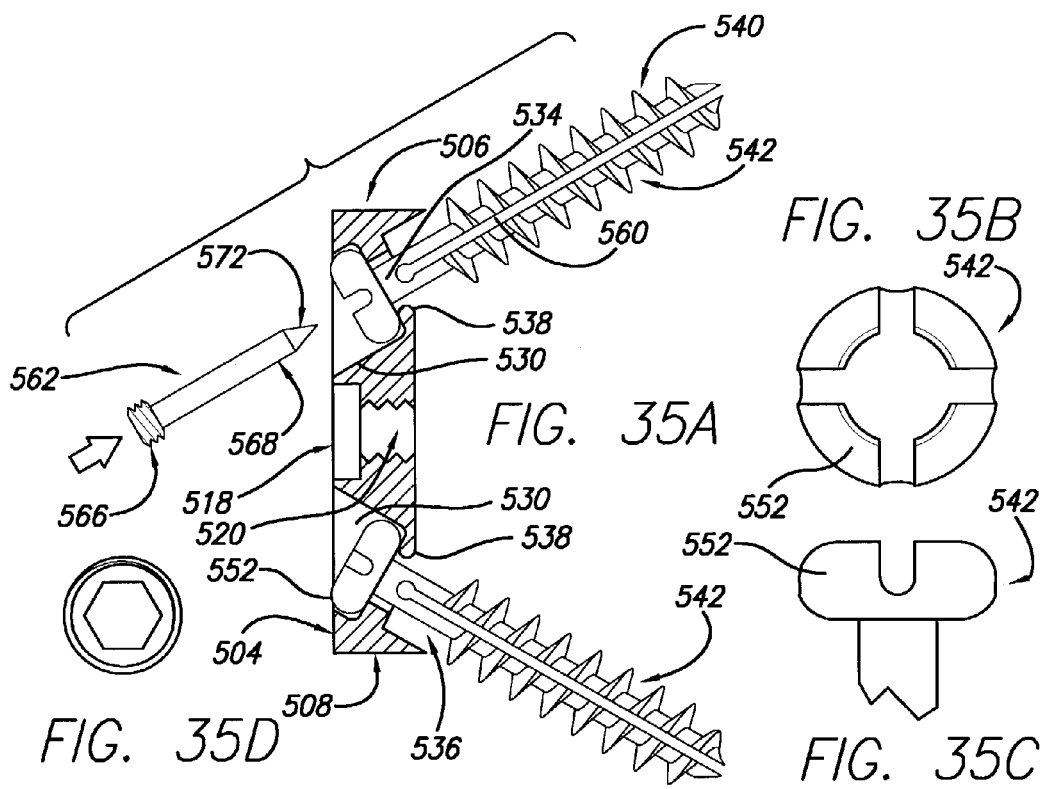
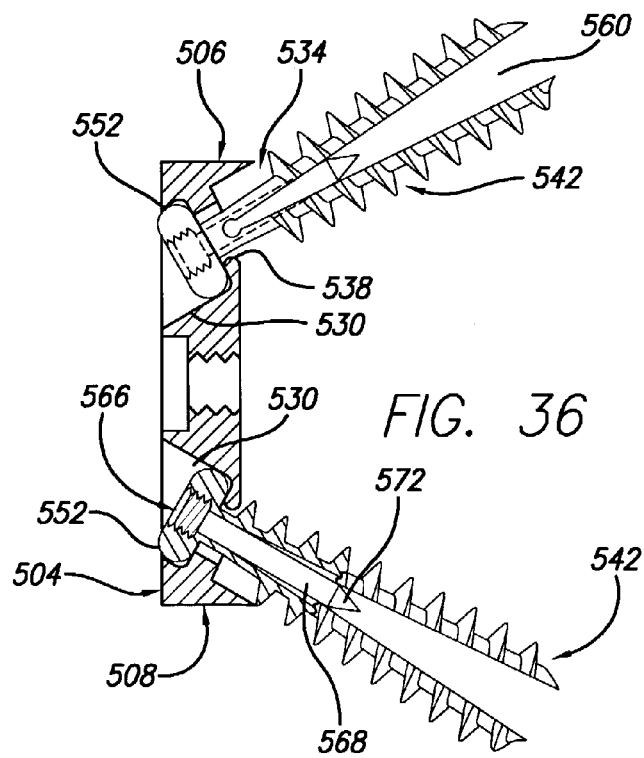

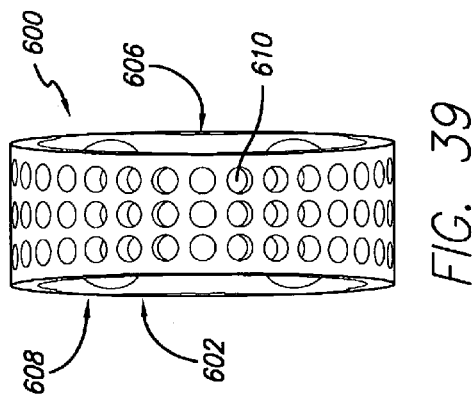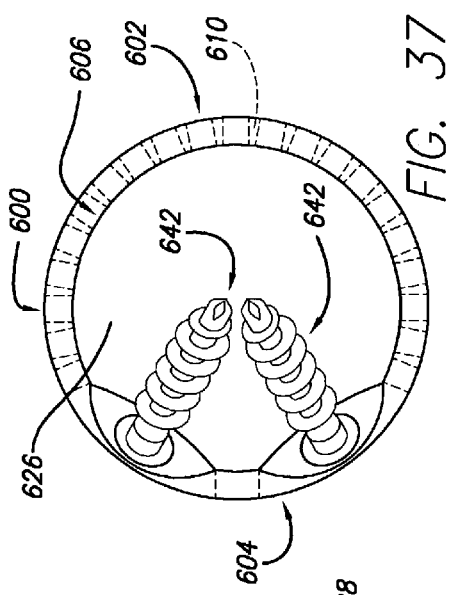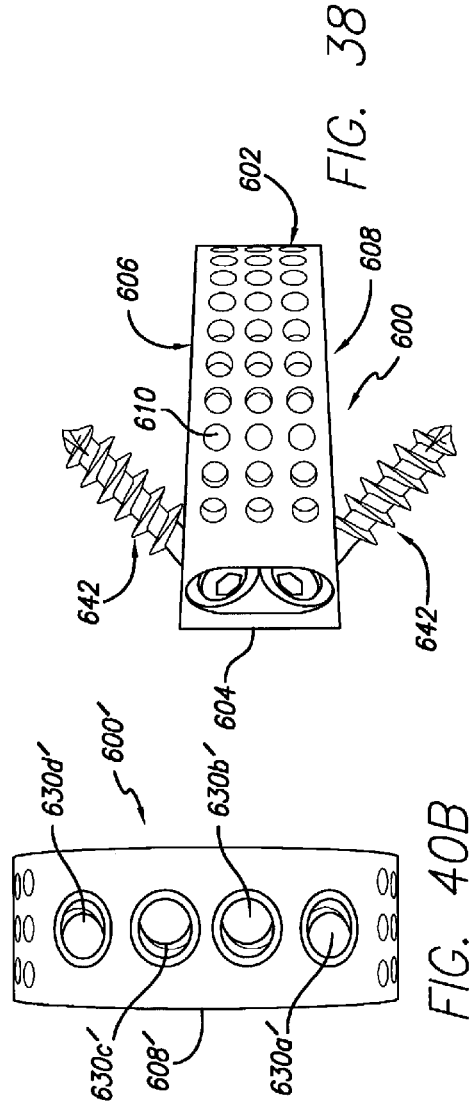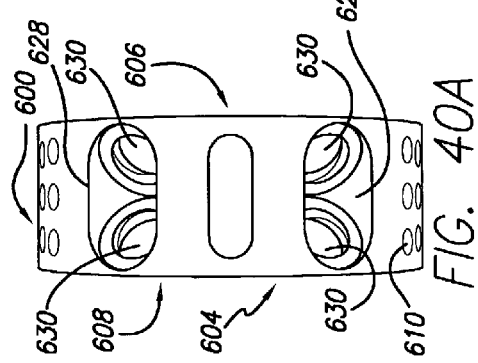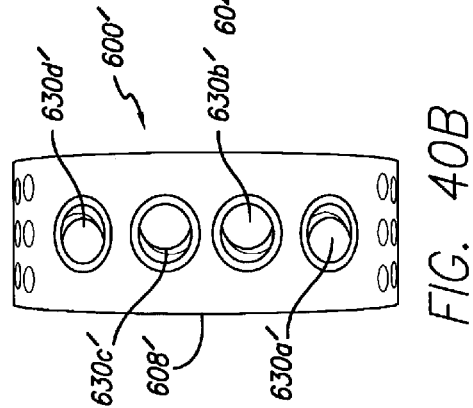

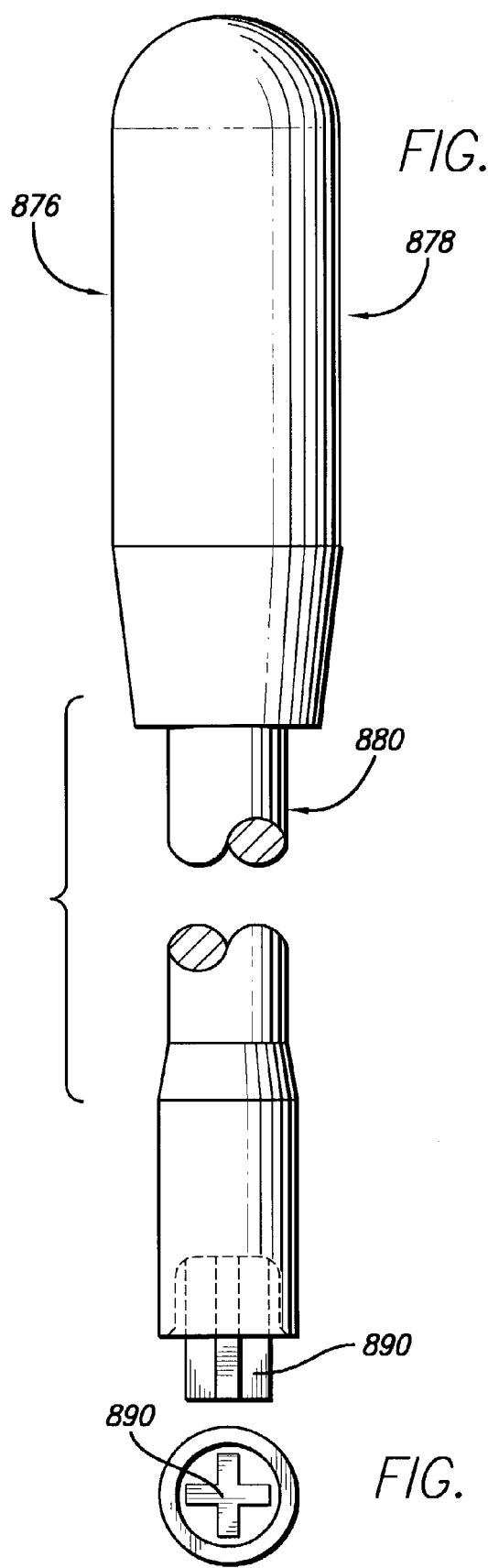
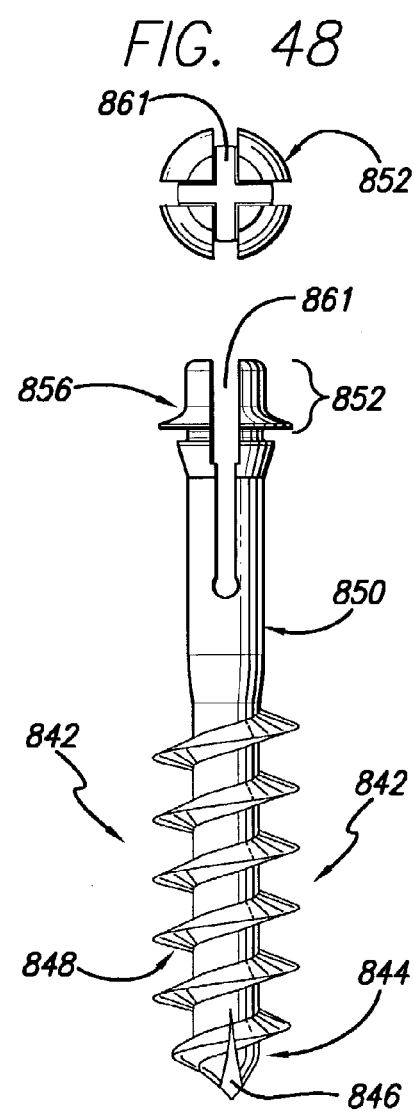
FIG. 47A
FIG. 47B
FIG. 48
FIG. 49

INTERBODY SPINAL FUSION IMPLANTS WITH END CAP FOR LOCKING VERTEBRAL BODY PENETRATING MEMBERS

RELATED APPLICATION

This application is a continuation of application Ser. No. 10/310,522, filed Dec. 5, 2002, which is a divisional of application Ser. No. 09/565,392, filed May 5, 2000, now U.S. Pat. No. 6,558,423, issued May 6, 2003, which claims the benefit of application Ser. No. 60/132,665 filed May 5, 1999 and application Ser. No. 60/133,214 filed May 7, 1999, all of which are incorporated by reference herein.

BACKGROUND

1. Field of the Invention

The present invention relates generally to interbody spinal fusion implants. Implants, artificial or natural, are placed at least in part within a disc space and in contact with each of the vertebral bodies adjacent that disc space for spacing apart and aligning those vertebral bodies and for allowing for the growth of bone in continuity from vertebral body to adjacent vertebral body through said implant.

2. Description of the Related Art

Some of the degenerative conditions that affect the spine may be so severe as to require surgical intervention. For example, a disc herniation may compress the spinal cord and/or nerve roots and cause pain, loss of function, and even complete paralysis of the legs with loss of bowel and bladder control. The correct treatment for such conditions is the removal of the offending discal tissue.

Sometimes, for a variety of reasons including the removal of disc material, the spine may become unstable (too much motion) at any given level. Historically, this has been treated by fusion, the joining together permanently of the unstable vertebrae via a bridge of bone so as to eliminate all motion along that portion of the spine.

To achieve fusion, bone or bone like substances are applied between two (or more) separate and distinct bones to induce bony bridging therebetween. When such procedures are successfully performed between vertebral bodies, an interbody fusion results. The shared bone in the area previously occupied by an intervertebral disc is referred to as an interbody fusion.

When a spinal surgeon seeks to perform an interbody fusion, the spine may be accessed from a variety of directions. If the surgeon elects to approach the spine anteriorly, this generally requires severing and/or removing substantial portions of the anterior longitudinal ligament over the operated area. The anterior longitudinal ligament is positioned along the anterior spinal surface and prevents hyperextension of the spine as an individual bends backward. Because the anterior longitudinal ligament covers the anterior spinal surface, the surgeon must cut through this tough ligament to access the disc space therebelow, compromising the stability of the spine. Specifically, the anterior longitudinal ligament is generally lax, except when an individual leans backward, then the ligament acts as a tension band resisting elongation. If the anterior longitudinal ligament is damaged, there is no check on that spinal movement and the vertebral bodies may detrimentally angulate.

Without a functional anterior longitudinal ligament, the patient may damage an implant(s) placed into a disc space to facilitate interbody fusion of the adjacent vertebral bodies. The implant may crush into or erode into, the adjacent vertebral bodies as the disc space opens anteriorly and crushes down posteriorly when the patient bends backwards. The vertebrae may rock together posteriorly and open anteriorly, thus dislodging the implant. Accordingly, in at least any spinal surgery requiring access to the disc space through the anterior longitudinal ligament, there is a need to functionally reconstruct the anterior longitudinal ligament to preserve stability about the disc space to be fused. Stability of the spine across the disc space to be fused is beneficial for achieving fusion.

In order to perform anterior interbody spinal fusion, a significant amount of disc material is removed from the interspace to be fused. After removing the disc material, the disc space is filled with an implant, which generally includes bone or bone in combination with a reinforcing structure, such as an artificial (other than bone) interbody spinal fusion implant. Because of the forces and motions occurring through the spine, it is not uncommon for such implants to dislodge, thereby causing a failure of surgery and possibly warranting further surgery to correct the problem and to again attempt interbody fusion.

Metal hardware outside the disc space affixed anteriorly to the vertebral bodies adjacent the disc space to be fused is useful to ensure the stability of the spine during the fusion period. Those skilled in the art have shown great reluctance to utilize such hardware because of the potential for the hardware to impinge on vital body structures, such as the aorta, vena cava, or great iliac vessels. The rupture of any of these body structures could cause sudden death. A rupture may occur late after surgery due to the pulsing of an artery against the metal hardware resulting in the eventual erosion and rupture of the artery. Further, metal applied to the outer surfaces of the vertebral bodies may become loose. For example, a screw may back out from repeated bodily movements, leading to the above-described situation.

Therefore, there is a need for an implant that is resistant to dislodgment and functionally substitutes for the anterior longitudinal ligament at the level to be fused, without protruding from the spine.

SUMMARY OF THE INVENTION

According to the present invention, an improved interbody spinal fusion implant is provided. The implant has structure that functionally substitutes for a damaged anterior longitudinal ligament following an anterior implant procedure. The present invention is not limited to functionally reconstructing the anterior longitudinal ligament, however, and also is useful for increasing the stability of the implant, decreasing the mobility of the adjacent vertebrae to be fused together, increasing and more evenly distributing the compressive loads across the fusion site, and mitigating the generation of undesirable localized excessive peak loads; and thus is of great benefit for implants inserted into the disc space posteriorly or laterally as well as anteriorly.

Existing interbody spinal fusion implants do not adequately addresses the above described broad needs or the need to functionally reconstruct the anterior longitudinal ligament, which to be useful must be done in a way that can assure the safety of the great blood vessels. The present teachings provide the structure by which implants may be constructed or existing implants may be modified to take advantage of the improvements of the present invention.

Implants that may be modified to incorporate the present teaching are those interbody implants adapted for placement within a disc space of the human spine between adjacent vertebral bodies, which implants have surfaces for contacting each of the adjacent vertebral bodies and structure therethrough, such as opening(s), to allow for the growth of bone from vertebra to vertebra through the implant. Such implants, inter alia, include generally rectangular implants such as disclosed in U.S. Pat. No. 5,776,199 to Michelson; lordotic interbody spinal fusion implants such as disclosed in U.S. Pat. No. 5,609,635 to Michelson; threaded cylindrical spinal implants such as disclosed in U.S. Pat. No. 5,860,973 to Michelson; thin-walled, perforated, threaded, hollow cylindrical implants such as disclosed in U.S. Pat. No. 5,015,247 to Michelson; and thin-walled, multiperforated partially cylindrical and cylindrical implants such as disclosed in U.S. Pat. No. 5,785,710 to Michelson. U.S. Pat. Nos. 5,776,199; 5,609,635; 5,860,973; 5,015,247; and 5,785,710 are incorporated herein by reference. The present invention and any or all of its parts may be constructed out of any material appropriate for the described purpose including, but not limited to, cortical bone, surgical quality metals, ceramics, bioresorbable and non-resorbable plastics and composites.

BRIEF DESCRIPTION OF THE DRAWINGS

FIG. 1 is a top plan view of a first embodiment of the implant of the present invention.

FIG. 2 is a trailing end view of the implant of FIG. 1.

FIG. 3 is a leading end view of the implant of FIG. 1.

FIG. 4 is a side elevational view of the implant of FIG. 1, including opposed bone screws.

FIG. 5 is a trailing end view of the implant of FIG. 4 with screws and screw locks installed.

FIG. 6B is a side elevational view in partial cross section of the distal end of the driver of FIG. 6A in accordance with its method of use with an implant shown as a portion in cross section, bone screw, and lock in cross section.

FIG. 7 is a top plan view of a second embodiment of an implant in accordance with the present invention.

FIG. 8 is a leading end view of the implant of FIG. 7.

FIG. 9 is a trailing end view of the implant of FIG. 7.

FIG. 10 is a side elevational view of the implant of FIG. 7, including opposed bone screws.

FIG. 11 is a trailing end view of the implant of FIG. 10 with the screws locked.

FIG. 14 is a top plan view of a third embodiment of an implant in accordance with the present invention.

FIG. 15 is a side elevation view of the implant of FIG. 14 with opposed bone engaging screws and screw lock.

FIG. 16 is a leading end view of the implant of FIG. 14.

FIG. 17 is a trailing end view of the implant of FIG. 14.

FIG. 18 is a trailing end view of the implant of FIG. 15 with opposed bone engaging screws and screw lock.

FIG. 19 is a side elevation view of a bone screw lock.

FIG. 20 is a side elevation view in partial cross section through the rear wall of the third embodiment implant with the bone screws and screw lock in place.

FIG. 21 is a top plan view of the fourth embodiment of an implant in accordance with the present invention.

FIG. 22 is a leading end view of the implant of FIG. 21.

FIG. 23 is a trailing end view of the implant of FIG. 21.

FIG. 24 is a side elevation view of the fourth embodiment implant with opposed bone engaging screws.

FIG. 25 is a trailing end view of the implant of FIG. 24 with screws and screw locks in place.

FIG. 30 is a top plan view of a fifth embodiment implant in accordance with the present invention.

FIG. 31 is a side elevation view of the implant of FIG. 30, with opposed locked bone screws and locks in place.

FIG. 32 is a trailing end view of the implant with screws and locks of FIG. 31.

FIG. 33 is a leading end view of the fifth embodiment implant.

FIG. 34 is a side perspective view of the fifth embodiment implant.

FIG. 35A is a side elevation view and partial cross section through the rear wall of the fifth embodiment implant, with bone screws, and a lock positioned for engagement with a bone screw.

FIG. 35B is a top plan view of a bone screw.

FIG. 35C is a side elevation view of a bone screw head.

FIG. 35D is a top plan view of a screw lock.

FIG. 36 is a side elevation view and partial cross section through the rear wall of the fifth embodiment implant with locks engaged with the bone screws.

FIG. 37 is a top plan view of a sixth embodiment of an implant in accordance with the present invention, with bone screws.

FIG. 38 is a side elevation view of the sixth embodiment implant with screws of FIG. 37.

FIG. 39 is a leading end view of the sixth embodiment implant.

FIG. 40A is a trailing end view of the sixth embodiment implant.

FIG. 40B is a trailing end view of an alternative sixth embodiment implant.

FIG. 47A is a side elevation view in partial ghost of a screwdriver for use with the self-locking screw of FIGS. 48 and 49.

FIG. 47B is a bottom end view of the distal portion of the driver of FIG. 47A.

FIG. 48 is a top plan view of the head portion of a self-locking screw of FIG. 49.

FIG. 49 is a side elevation view of the self-locking screw of FIG. 48.

DETAILED DESCRIPTION OF THE DRAWINGS

Figure 6A:
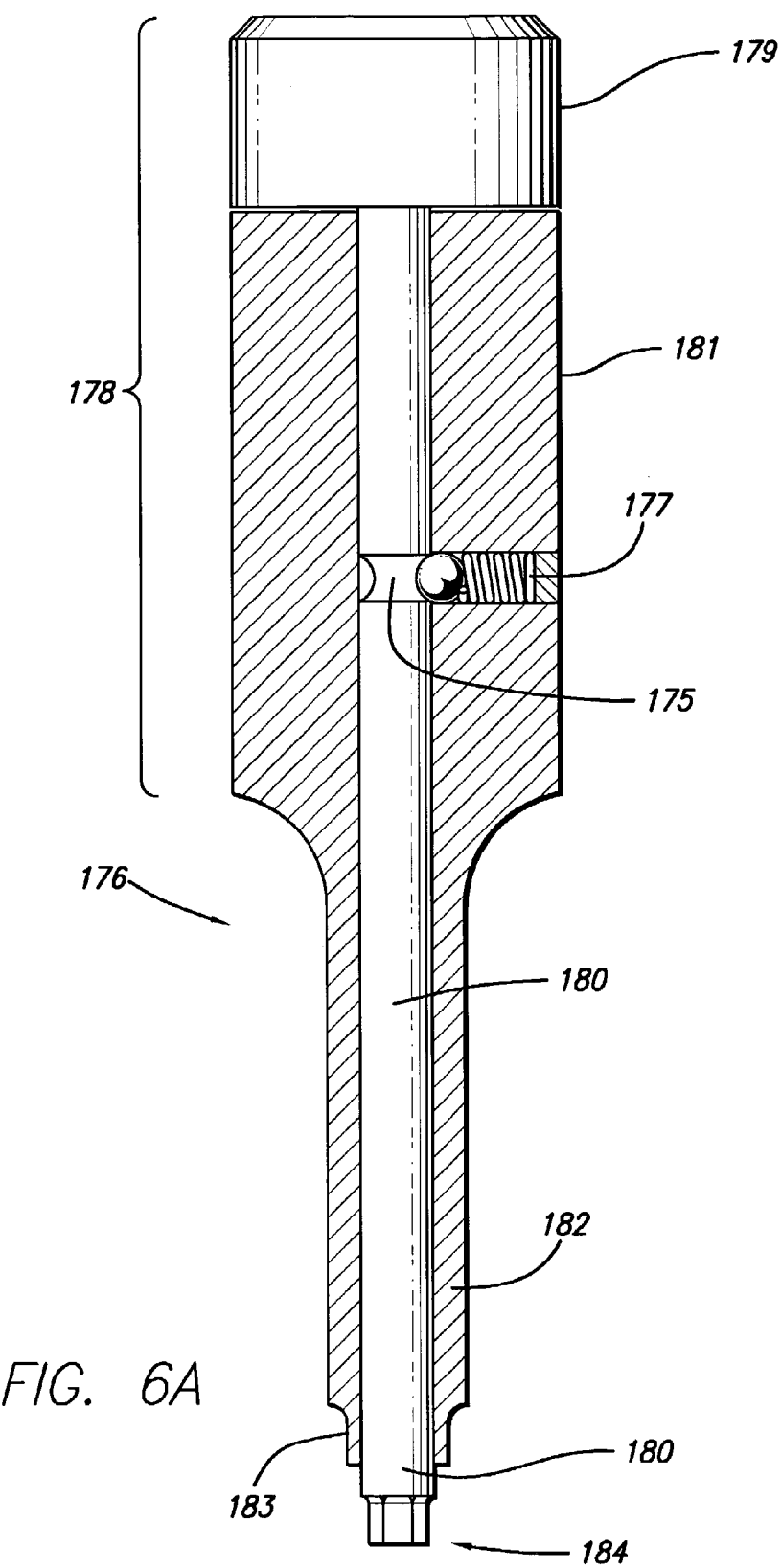
FIG. 6A is a side elevational view in partial cross section of a screw-lock driver.

The present invention relates first to implants to be placed within a human spine, at least in part, within a disc space between adjacent vertebral bodies, for the purpose of fusing together those two adjacent vertebral bodies across the intermediate disc space. Though not so limited, it is desirable that these implants allow for the growth of bone from vertebra to adjacent vertebra through the implants themselves. To this end, each implant, when inserted, will have an upper implant surface for engaging the upper of the adjacent vertebral bodies and an opposed lower implant surface for engaging the adjacent lower vertebral body. It is desirable that each of these opposed surfaces has at least one opening, and possibly a plurality of openings, sufficient in size, and in continuity with each other, to allow for the growth of bone from vertebral body to adjacent vertebral body through said implant. While not requisite, it is also desirable that these implants further be hollow to facilitate such bone growth through the implant.

The implants of the present invention differ from all prior art implants in that they are adapted to receive through their trailing ends at least a pair of appropriately sized opposed bone screws that can be directed at an appropriate angle, at least one each, into each of the adjacent vertebral bodies adjacent the disc space to be fused. In a further novel teaching of the present invention, these implants adapted to receive the opposed bone screws are further adapted also to receive bone screw locks, or in the alternative the screws are adapted to receive locks to lock the screws to the implants to prevent the backing out of the bone screws from the implants.

To the extent that such implants are hollow and have openings through the surfaces, those openings and those hollows can preferably be filled with fusion promoting substances, including substances that are osteogenic, osteo-inductive, or osteo-conductive, whether naturally occurring, or artificially produced. Such substances could include, but are not limited to, bone in any of its forms, whether naturally occurring or processed, hydroxyapatite, calcium phosphate compounds, bone morphogenetic proteins, and genetic materials coding for the production of bone. Various embodiments of the present invention show implants having a large hollow therein. While not requisite, it may be advantageous to have a large access-way to the implant hollow. By way of example, a cap may be used for closing all or part of the access-way.

The present invention implant including the screws and locks may be formed of any material suitable for their intended purpose. To that end, they can be made of a surgical quality metal such as titanium or one of its alloys, cobalt chrome, or any other surgical quality metal suitable for the intended purpose. The implant can be made of an appropriate ceramic, be it naturally occurring or artificially produced. The implant also can be formed of or include cortical bone. The implant can be formed of plastics or composites, for example, a carbon fiber plastic material or bioresorbable material. The implant can further comprise or be filled with, treated with, coated with, or used in combination with various fusion promoting substances, including but not limited to hydroxyapatite, calcium phosphate compounds, bone morphogenetic proteins, genetic materials coding for the production of bone, and a chemical substance to inhibit scar formation.

Shown in FIGS. 1 through 5 is a first embodiment of the present invention. Generally cylindrical, highly perforated, hollow interbody spinal fusion implant 100 has a leading end 102 and a trailing end 104. Leading end 102 has a threadable cap 112 having a drive aperture 114, and holes 110 for the through growth of bone and vascular access. At trailing end 104 is a box-like recess 118 for receiving an implant driver (not shown). Trailing end 104 of implant 100 also has a plurality of bone holes 110 and two more specialized openings 120 which are threaded for receiving a complimentary threaded member from a driver so as to allow the driver to rigidly affix to trailing end 104 of implant 100. Trailing end 104 also has bone screw receiving holes 130, which additionally could be used to receive an implant driver. It can readily be appreciated that the trailing end of this implant or any implant embodiment of the present invention in general can be adapted in a multitude of ways for cooperatively receiving an implant driver to make possible the insertion of the implant into a spine.

Implant 100 has an upper surface 106 and an opposed lower surface 108, each being adapted for placement into contact with one of the two adjacent vertebral bodies adjacent a disc space to be fused. Upper and lower surfaces 106 and 108 each have a plurality of openings 110 for the through growth of bone. The present invention includes any number or arrangement of openings so long as sufficient to work for the intended purpose. Upper and lower surfaces 106 and 108 also have an opening 134 and 136, respectively, for allowing the passage therethrough of a bone screw for further attaching implant 100 to each of the adjacent vertebral bodies. Openings 134, 136 are preferably shaped and formed so as to facilitate the insertion of bone screws 142 through the rear or trailing end 104 of implant 100 and in part through openings 134, 136. The heads 156 of screws 142 do not pass completely through openings 134, 136. Screws 142 pass out of implant 100 preferably at an angle of between 25° and 75° to the long axis of implant 100.

Opposed vertebral body engaging screws 142 are illustrated as having the preferred, but not requisite, cancellous-type thread 148 and a pointed tip 144 with cutting flutes 146 so as to allow screws 142 to be self-tapping. While any screw useful for the intended purpose is contemplated to be within the scope of the present invention, a self-tapping screw with a cancellous-type thread pattern over a significant portion of the shaft, with a smooth shaft proximally corresponding to the portion within the implant, and a head that can be lagged against the implant is particularly preferred for its advantages. The screw head 156 has a drive recess 154, here shown as a hexagon.

FIGS. 6A and 6B show a driver 176 for use with the first embodiment of the present invention. Driver 176 comprises a handle 178, having an upper handle portion 179 and a lower handle portion 181. Upper handle portion 179 is attached to a central shaft 180 which terminates in a hex drive tip 184. Shaft 180 passes coaxially through handle 178 which extends downward to form a second shaft 182 that houses shaft 180 and terminates distally in a second hexagonal tip 183. An annular groove 175 in shaft 180 receives a ball and spring detent 177 to hold handle 181 and contiguous shaft 182 in selective position relative to handle 179 and contiguous shaft 180.

As can be appreciated from FIG. 6B, in use hexagonal driver tip 184 of shaft 180 is utilized to insert through the trailing end 104 of implant 100 bone screw 142 by means of a hex depression 154 in bone screw head 156. Once screw 142 is fully inserted through the opening 130 in trailing end 104, the enlarged portion of the head 156 is blocked from passing fully through implant 100 by a retaining flange 138 of the implant. At this point, it is possible to cause the vertebral body into which the threads of screw 142 are implanted to be lagged towards, that is to be compressed to, the implant surface and particularly towards trailing end 104 of implant 100 by further rotating screw 142. Once the optimal compression has been obtained as determined by the surgeon at the time of surgery, with tip 184 of shaft 180 still engaged with screw head 156 within depression 154, the surgeon then utilizes shaft 180 as a centering post and separates handle portion 181 from handle portion 179 by pressing downward. This downward pressure causes the detent ball and spring 177 to be forced out of annular groove 175 and allows second shaft 182 to move downward, taking with it lock 162 which was engaged to driver 176 prior to engaging driver 176 to bone screw 142.

Lock 162 is circumferentially threaded with threads 172. When second shaft 182 is advanced distally along shaft 180, lock 162 contacts trailing wall 104 of implant 100, such that threads 172 of lock 162 can be threaded into the receiving threads 140 of implant 100. In this example, it can be appreciated that opening 130 is not fully threaded for its entire depth, but only sufficient to allow lock 162 to become generally flush with trailing wall 104, at which point lock 162 can be quite rigidly tightened against the unthreaded portion of opening 130, which acts as a stop, preventing any further movement of lock 162 into opening 130. By binding lock 162 to trailing wall 104 of implant 100 and making lower surface 174 of lock 162 concave, allowance is made for motion of screws 142 relative to implant 100. This allows the surgeon some freedom of choice in positioning screws 142 and in selecting the direction of the force vector to be generated relative to implant 100. It further allows for some settling of the vertebrae should that occur over time without the danger of the screws acting to hold the vertebrae from implant 100.

Alternatively, by any number of structural configurations, such as by way of an example an interference fit between screw head 156 and implant opening 130, or by way of more deeply threading the opening 130, or by flattening the top of the screws and making the circumferential perimeter flush to the lock, or by allowing the lock to contact the screw head, later motion of the screw can be prevented. Said differently, while the present example shows how to allow for variability in the screw's placement and provides for later movement of the screw as might occur with settling, in the alternative, the path of the screw through the implant can be rather narrowly defined, and any angular motion of the screw relative to the implant can be prevented.

FIGS. 7 through 13 show a second embodiment of the present invention. Implant 200, though similar to implant 100, differs from implant 100 in that the sides have been tangentially removed and the remaining upper and lower arcuate portions have been wedged apart, such that trailing end 204 is taller than the leading end 202. The tangential truncation of the sides allows two implants 200 to be placed side-by-side, such that the combined width of the two implants is significantly less than the combined height of the implants.

The convergence of upper and lower surfaces 206, 208 from trailing end 204 to leading end 202 is beneficial for inducing lordosis when implant 200 is inserted across the disc space between two adjacent vertebrae from anterior to posterior. Without in anyway departing from the present invention, the implants shown herein by way of example only, can be modified for posterior insertion, in which case the upper and lower surfaces may be generally convergent from the leading end to the trailing end.

Implant 200 has a leading end 202, having a plurality of holes 210 therethrough for the through growth of bone and vascular access. Implant 200 does not have a removable cap as did implant 100, relying rather on large opening 224 which may be present on each side, or one side only to provide access to the hollow interior 226 of implant 200 for the purpose of loading implant 200 with fusion promoting substances. The implant upper and lower surfaces 206 and 208, respectively, each have at least one and preferably a plurality of bone holes 210, and similar to implant 100, a series of forward facing annular ratchets for engaging the vertebral bone. Upper surface 206 and lower surface 208 have openings 234 and 236, respectively, for conducting therethrough bone engaging screws 242. When implant 200 is implanted, screws 242 are introduced through trailing end 204 of implant 200. Trailing end 204 has a pair of opposed bone screw receiving holes 230 angled so as to direct screw 242 introduced through trailing end 204 of implant 200. Holes 230 receive screw 242, which passes therethrough and into each of the adjacent vertebral bodies. Screw 242 preferably is at an angle to the longitudinal axis of implant 200 and more preferably at an angle of from 25° to 75°. Implant 200 has a plurality of bone holes 210. Situated intermediate to opposed bone screw receiving holes 230 is a lock 262 having a head portion 256 with a hex well 264 therein, and opposed concave portions 272. It should be understood that various driver engaging structures useful for the intended purpose are anticipated and within the scope of the present invention.

Figure 12:
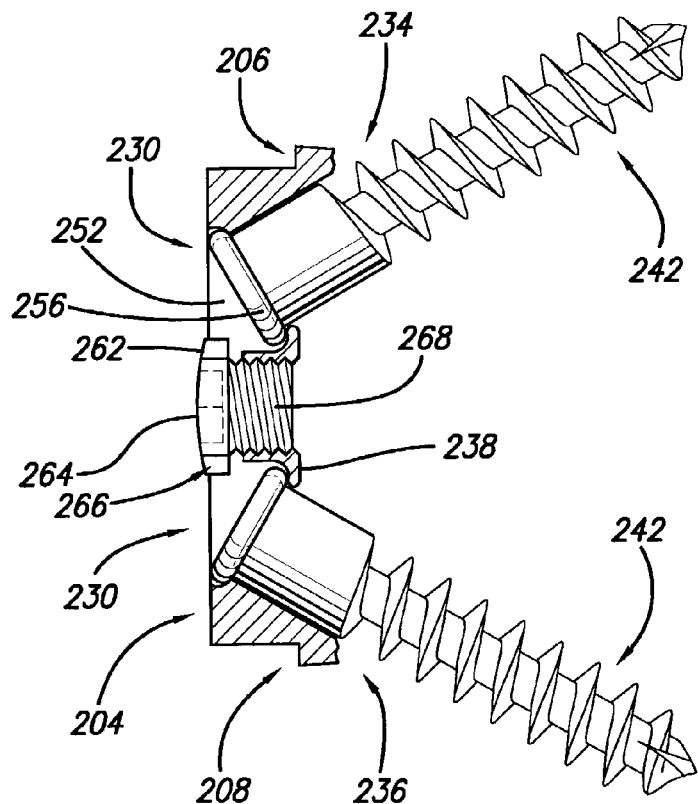
FIG. 12 is a cross sectional side view of an implant rear wall, with opposed bone screws, and a preinstallable lock in the open position.

As shown in FIGS. 9 and 12, when lock 262 is one-quarter turn short of being fully tightened, openings 230 are fully open for receiving opposed bone screws 242.

Figure 13:
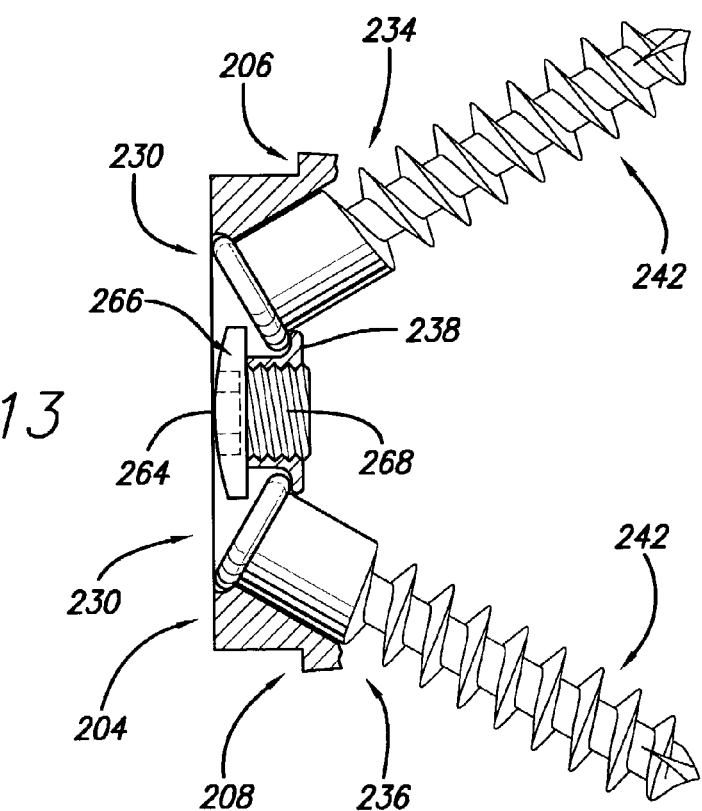
FIG. 13 is a cross sectional side view of an implant rear wall, opposed bone screws, and with the locking element of FIG. 12 in the locked position.

As shown in FIGS. 11 and 13, once opposed bone screws 242 have been installed, lock 262 can be further tightened by turning it 90 degrees until head 264 bottoms out against implant trailing end 204, thereby allowing the locking screw to be solidly tightened to implant 200.

In FIGS. 9 through 13, it can be seen that a pair of bone screws 242 can be inserted through openings 230 in trailing end 204 of implant 200, such that heads 256 of screws 242 are restrained within implant 200 by the contact of the enlarged head 256 against flange portion 238 of implant 200. Threaded shaft 268 of lock 262 threads into the rear of implant 200.

It can be noted in FIGS. 11 and 13 that while screws 242 have freedom to move closer together to allow for settling, screws 242 cannot back out of implant 200 with lock 262 in place. As previously discussed, while this is considered preferable, implant 200 can be so constructed to prevent any angular freedom of screw 242 relative to implant 200. Further, implant 200 and lock 262 can be configured to cooperate to prevent any backward motion of screw head 256.

FIGS. 14 through 20 show a third embodiment of the present invention. Implant 300 is generally cylindrical and hollow with a thin outer wall that is highly perforated and carries a helical thread. This particular thread configuration is offered by way of example only, and the invention anticipates and includes any thread suitable for the intended purpose. Further it is understood that a thread can be so formed that it becomes difficult to define the thread from the outer wall, such that the outer surface of the implant is, in essence, the peaks and valleys of the thread. It is further understood that while the thread shown here is generally continuous and helical, the thread also could be interrupted.

Implant 300 has a leading end 302 having a threadable cap 312 with a plurality of bone holes 310 and a central hex aperture 314 for receiving a driver. Alternative embodiment implants may be open at their leading ends, trailing ends, or both, or may be closeable or partially closeable with other than a threaded cap. Implant 300 has an upper bone engaging surface 306 and an opposed lower bone engaging surface 308. Intermediate upper and lower surfaces 306 and 308, implant 300 has side surfaces identical to surfaces 306 and 308. Each of these four surfaces have an opening such as 334 and 336, allowing for the passage of bone screw 342 therethrough. This arrangement allows for implant 300 to be inserted into the implantation site by being threaded into the spine until fully inserted and then properly aligned by quarter-turn increments. As implant 300 is advanced with every one-quarter turn, there is the opportunity to properly align a pair of opposed bone screws 242 through upper and lower surfaces 306 and 308. It can be appreciated that implant 300 is highly perforated with a multitude of holes 310, situated over each of the implant surfaces, though as few as one adequately sized hole per surface could suffice.

With attention to FIGS. 17 and 18, it can be appreciated that trailing end 304 of implant 300 has a threaded central aperture 320 located within a partially rectangular recess 318 for threadably engaging an implant driver adapted to interdigit and to threadably connect thereto for rotating the implant, both clockwise and counterclockwise while simultaneously either pushing or pulling as desired by the surgeon. Trailing end 304 has four symmetrically disposed bone screw receiving holes 330. Once a pair of opposed bone screws 342 have been inserted through trailing end 304 of implant 300 and into the adjacent vertebral bodies and sufficiently tightened, lock 362 is inserted into threaded aperture 320 by means of a driver placed into hex well 364 and then tightened down to the back of implant 300. A pair of unused bone screw holes are then available as bone holes similar to 310. FIG. 19 shows the structure of lock 362 having an enlarged head portion 366, a threaded shaft 368, and a shoulder 372 to allow lock 362 to be tightened against implant 300.

FIG. 20 shows lock 362 in use, where it can be appreciated that head portion 352 of screw 342 is prevented from passing through implant 300 by retaining flange 338 at the base of hole 330. It can also be appreciated that when lock 362 is fully tightened, portion 372 of head 366 can be tightened against implant 300 itself so as to, as previously described, allow for some convergent motion of the bone screws in the event of vertebral settling.

FIGS. 21 through 29 show a fourth embodiment of the present invention. Implant 400 has a convex leading end 402 and an opposite trailing end 404, here shown as having a generally straight mid-portion with radiused junctions to the side walls of implant 400. In the alternative, trailing end 402 of implant 400 could be generally convex and, still further, could be curved so as to generally conform to the contour of the anterior vertebral body in order to sit in close approximation thereto, without the need to be significantly recessed. In another alternative, trailing end 402 could be curved so as to extend significantly beyond the anterior cortical margins of the vertebral bodies to be fused.

Both leading end 402 and trailing end 404 of implant 400 are highly perforate to allow for vascular access to hollow interior 426 of implant 400, and to allow for the growth of bone therethrough. While the present invention does not require the presence of such openings, these openings are considered highly desirable. Any variation in particular configuration of such openings, or their arrangement, and number, so long as useful for the intended purpose, are also within the scope of the present invention. Implant 400 has opposed upper and lower vertebral body engaging surfaces 406 and 408, respectively, which preferably have surface irregularities serving to both increase the surface area of the implant and the ability of the implant to engage the adjacent vertebral bodies, thereby enhancing their stability. Implant upper and lower surfaces 406 and 408 have large windows or slots 424 therethrough, each in communication with the central hollow chamber 426 of the implant and each forming a direct path to its counterpart on the opposite surface through implant 400.

As shown in FIGS. 23 and 25, trailing end 404 of implant 400 has, in addition to the plurality of bone holes 410, two specialized common holes 428, each containing two further holes 430. Each of holes 430 is adapted to receive a bone screw 442 through trailing end 404 of implant 400 at an angle such that the bone screw would be directed first through trailing end 404, then through either one of upper or lower vertebral bone engaging surfaces 406 and 408 of implant 400, and finally into the vertebral body itself at an angle preferably between 25° and 75°. Holes 430 and common hole 428 are angled apart so as to assure that a pair of bone screws 442 inserted therethrough will be directed one each into each of the vertebral bodies adjacent the disc space containing implant 400. Trailing end 404 also has a central threaded aperture 420 for receiving a threaded member for cooperatively engaging an implant driver. Other ways of coupling the implant and implant driver can be readily anticipated and are within the scope of the present invention.

As can be appreciated from FIG. 25, trailing end 404 of implant 400 is adapted to receive a total of four bone screws 442 deployed in upwardly and downwardly projecting opposed pairs, and further to receive into common holes 440 threaded lock members 462, preventing screws 442 from backing out.

As can be appreciated from FIG. 24, implant 400 has a height greater at its trailing end 404 than at its leading end 402, such that the implant itself is lordotic, or capable of inducing a lordotic angulation between adjacent vertebral bodies when inserted into the spine from an anterior to posterior approach. The present invention also includes such implants where the upper and lower surfaces 406 and 408 are parallel rather than convergent and, still further, where the upper and lower surfaces 406 and 408 are divergent from the trailing end to the leading end, for use from a posterior to anterior approach.

When the implant as shown in FIG. 24 is inserted from anterior to posterior between the adjacent vertebral bodies, any tendency for implant 400 to back out of the implantation site created across the disc space due to the wedge-shaped contour of the implant is resisted by both the forward facing ratchetings 422 and the trajectory of screws 442. Bone screws 442 further serve to pull the vertebral bodies to upper and lower implant surfaces 406 and 408 so as to increase the compressive load thereon and mitigate against a loss of that compressive load or a distraction anteriorly which might otherwise occur if a patient were to bend back and forth or otherwise extend. Consistent with the preferred, highly perforate nature of implant 400, the side walls of the implant also have holes 424 therethrough to allow for vascular access and the through growth of bone.

Figures 26, 27:
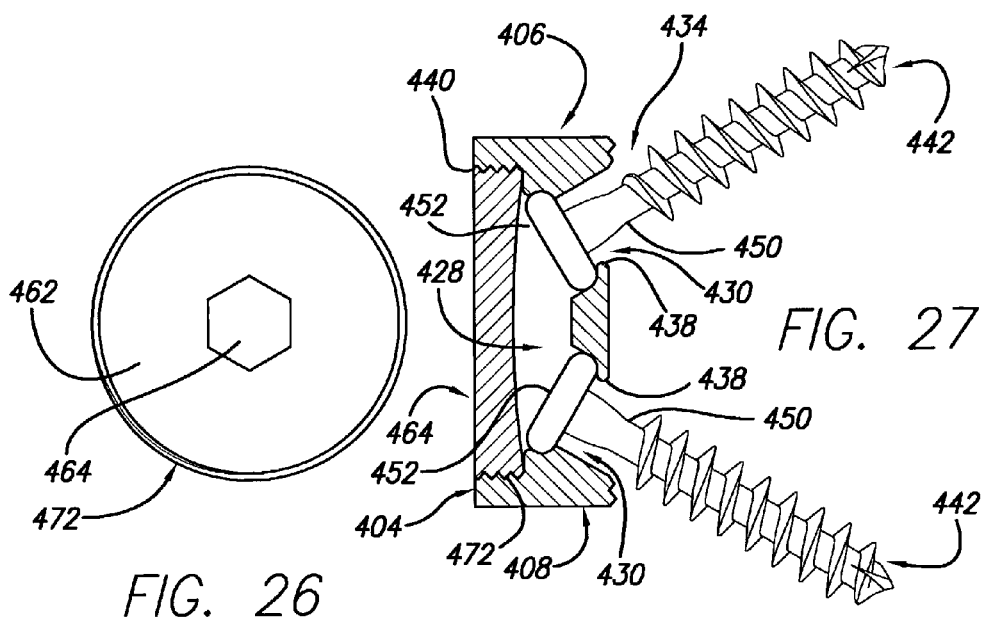
FIG. 26 is a top plan view of the screw lock of FIG. 25.
FIG. 27 is a side elevation view in partial cross section through a portion of the rear wall of the fourth embodiment implant, with opposed bone screws, and lock.

FIGS. 26 and 27 show details of holes 430 through trailing end 404 of implant 400 in relation to lock 462 and a pair of opposed bone screw 442. In this example, bone screws heads 452 are sufficiently large that they are not able to pass through flange 438 and are thereby retained within the rear portion of implant 400. Immediately distal to heads 452 of screws 442 is a smooth shaft portion 450 of a lesser cross sectional dimension than hole 430 which, in combination with the available space within common hole 428 between screw head 452 and lock 462, allows for bone screw 442 to operate as a lag screw, but, nevertheless, be capable of some variability in its positioning and ability to move closer to implant 400 in the event of subsequent settling of the vertebral bodies towards implant 400. In this embodiment, lock 462 takes the form of a disc with a threaded side wall 472, capable of threadably engaging threads 472 within common hole 428. Lock 462 comprises a hex receiving opening 464 for rotationally driving lock 462. In a preferred variation, hex opening 464 or other equivalent driver receiving configuration, is the same as that of head 452 of screw 442.

Figures 28, 29:
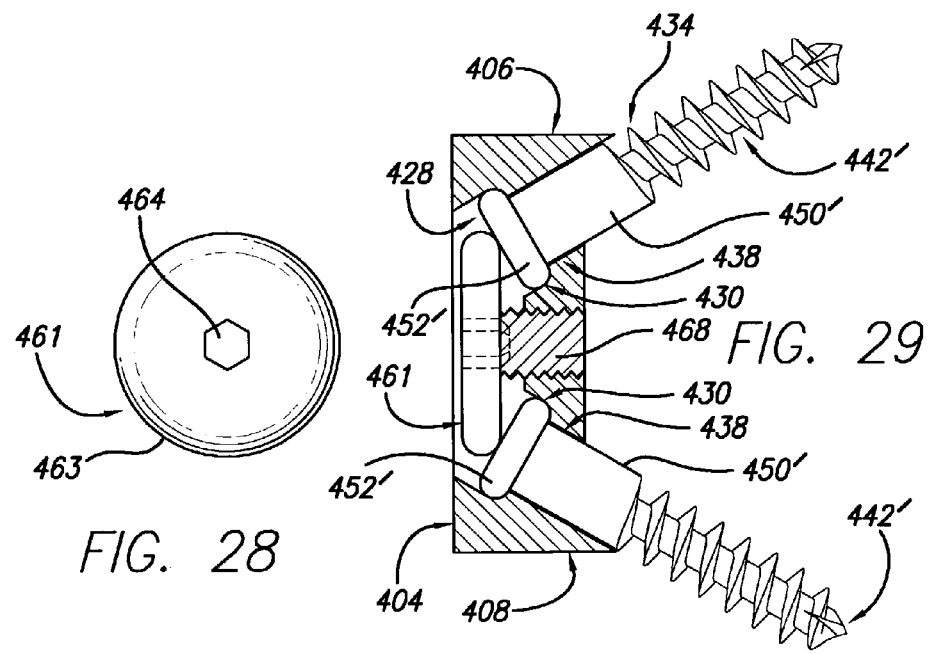
FIG. 28 is a top plan view of an alternative lock.
FIG. 29 is a side elevation view and partial cross section through the rear wall of the fourth embodiment implant with the bone screws and alternative lock of FIG. 28 in place.

Turning now to FIGS. 28 and 29, an alternative implant screw and lock arrangement is demonstrated for use with implant 400, or as with the lock and screw configuration of FIG. 27 with any of the other embodiments of the present invention as may be appropriate. To that end, it should be appreciated that the implants shown herein are by way of example only and without limitation to the various combinations and permutations of the various screw, lock, and implant configurations shown, as well as the substantial equivalent thereof which are anticipated and claimed to be within the scope of the present invention.

Lock 461 differs from lock 462 in that extending from head portion 463 is a threaded shaft 468 for threading into a threaded hole between opposed holes 430 within common hole 428 of implant 400. Unlike the mechanism illustrated in FIG. 27 where cap 462 tightens against the internal implant wall rather than locking against the screw heads themselves, thereby permitting motion, head 463 of lock 461 tightens against heads 452' of screws 442'. Screws 442' differ from screws 442 in that the smooth proximal shaft portions 450' are adapted to form an interference fit with the passageway through the rear portion of implant 400 and thereby allow the screws to have a precise trajectory while being rigidly locked to the implant. It should be appreciated then that FIGS. 27 and 29 each teach a structure by which an implant of the present invention can be constructed so as to either cause the screws passing therethrough to have a fixed trajectory or a variable angle placement. Further taught is structure for permitting implants to either allow for, or to prevent post-deployment angular motion of the bone screws relative to the implant after the screws have been locked therein; or to allow for but one degree of freedom of the locked screws for the settling or the coming closer together of the adjacent vertebrae. Various ways of achieving such structures are shown herein and may be combined in various ways with various embodiments of the implants shown or their substantial equivalents without departing from the scope of the present invention.

FIGS. 30 through 36 show a fifth embodiment of the present invention. Implant 500 is an improvement upon the implants described in pending Michelson U.S. application Ser. No. 09/106,216 incorporated herein by reference. These implants have been adapted to have bone screw receiving holes 530 in posterior walls of trailing end 504 and, in each of the opposed upper and lower surfaces 506 and 508, respectively, holes 534 and 536 for transmitting bone screws therethrough, respectively. Trailing end 504 also comprises a rectangular slot 518 for engaging a rectangular member of an implant driver insertable therein. A threaded hole 520 located within slot 518 allows the implant driver to further be secured to the implant by threadably engaging the implant therethrough. This allows the implant, when properly engaged to the driver, to be rotated either clockwise or counterclockwise and simultaneously be pushed or pulled at the discretion of the surgeon.

While not requisite, in a preferred embodiment, implant 500 is highly perforate and has holes 510 for vascular access and bone through growth through its leading end 502, side walls, and upper and lower surfaces 506 and 508. While trailing end 504 is herein shown lacking additional bone holes, this has been done to emphasize that such openings are only preferred, not requisite. As herein before stated, the particular shape, number, and arrangement of the holes are all within the scope of the present invention so long as they are appropriate for their intended purposes.

Leading end 502 of implant 500 is herein shown with a cap 512, which is threaded and removable, and can be operated by a driver engaging hex opening 514. Cap 512 can be removed so that the hollow interior 526 of implant 500 can be compressibly loaded with bone. Cap 512 can then be screwed to the leading end 502 so as to prevent the gross extrusion of the osteogenic materials loaded under pressure within the implant while, nevertheless, providing for vascular access to the interior of the implant and bone growth therethrough. Further, cap 512 may provide structural reinforcement to the implant so as to provide enhanced strength.

Upper and lower surfaces 506 and 508 of implant 500 have a series of transverse fins 522 and interposed therebetween a plurality of bone slots and bone holes 510 for the growth of bone therethrough. Implant 500 as is described in copending U.S. application Ser. No. 09/106,216 is adapted to be inserted on its side and then, only after being fully inserted, rotated 90 degrees so that upper and lower surfaces 506 and 508 engage each of the adjacent vertebral bodies adjacent the disc space in which the implant has been implanted for fusion. Once implant 500 has been properly inserted, bone screws 542 are inserted through opposed holes 530 in trailing end 504 and through holes 534 and 536 in upper and lower surfaces 506 and 508, respectively, with one each passing into each of the vertebral bodies. As with various of the other embodiments of the present invention it is anticipated that the trailing ends of said implants need not have a trailing wall, but rather a generalized opening without departing from the scope of the present invention.

As shown in FIGS. 35A–36, bone screws 542 have a head 552 and at least a partially, cancellously threaded shaft which is longitudinally cleaved to form an expansion slit 560. Screws 542 may be self-tapping. It may be alternatively beneficial to pre-drill an appropriate opening with a drill placed through the implant and into the vertebral body for receiving screw 542. When screw 542 has been fully inserted, head 552 is prevented from further motion forward by retaining flange 538, and it is then possible to generate a compressive lag of the vertebral body against implant 500 with screw 542. A locking member 562, having a smooth shaft 568 terminating distally in tip 572 is then inserted through the drive opening in head 552 of screw 542 until portion 566 of lock 562 threadably engages within head 552. Then as lock 562 is threaded more deeply into head 552 of screw 542, point 572 wedges apart a conically tapered recess in the shaft of screw 542, thereby wedging apart the two portions of the shaft.

FIG. 35B is a top view of bone screw 542 of FIG. 35C. FIG. 35 shows the crossed or Phillips type driver receiving structure of one preferred embodiment of the present invention. A central opening in screw 542 is adapted to receive lock 562. FIG. 35D is a top view of lock 562 and shows a hex configuration of one preferred embodiment of the present invention for receiving a driver.

In FIG. 36, the opening of slot 560 is exaggerated to be more useful in demonstrating the function of this particular embodiment. Screw 542 may be constructed so as to take advantage of a proximal thread portion or other enlargement beyond the root diameter of the proximal shaft which can be utilized to form a lock against rearward migration of the screw as it contacts retaining flange 538. With or without such a feature, screw 542 can also rely on its spreadable nature to prevent backward migration of the screw. Other variations on this theme, such as the use of a screw with an expandable casing, or any type of expandable screw are clearly within the scope of the present invention, as are screws having a hollow head and shank portion for transmitting therethrough a second element which is designed to protrude from the screw at an angle and therefore lock the screw in place.

FIGS. 37 through 42 show a sixth embodiment of the present invention. Implant 600 may generally be round or oblong or comprised in the top view of both arcuate and linear portions, or arcuate portions of differing arcs of radii. In one variation of implant 600, upper and lower vertebrae engaging surfaces 606 and 608, respectively, are but the end surfaces of the perimeter wall of the implant itself. While upper and lower surfaces 606 and 608 could be generally parallel from leading end 602 to trailing end 604. In a preferred embodiment, trailing end 604 of implant 600 is taller than leading end 602 of implant 600, such that the opposed upper and lower surfaces 606 and 608 are converging from the trailing end to the leading end. This offers the advantage that when implant 600, which is adapted for insertion from anterior to posterior or from a position anterolaterally, is inserted, the end of the implant that Will face posteriorly will be of a reduced height. This makes the insertion of the implant into the space from anterior to posterior much easier as less initial distraction of the disc space between the adjacent vertebrae is required. Further, having opposed upper and lower surfaces 606 and 608 diverge from leading end 602 to trailing end 604 allows for further restoration of the normal lordotic angulation through the disc space between the adjacent vertebrae to be fused.

Implant 600 has a plurality of holes 610 located through its perimeter wall to allow for the growth of bone and vascular access therethrough. Implant 600 has a large central hollow 626 for containing fusion promoting substances such as bone and for allowing the fusion of vertebrae to adjacent vertebrae through the implant through area 626 and through the disc space. Implant 600 is adapted to receive opposed bone screws 642 for engaging each of the vertebral bodies adjacent the disc space into which the implant is implanted.

As shown in FIG. 40A, trailing end 604 of implant 600 has common holes 628 having opposed bone screw receiving holes 630. Holes 630 are not only angled away from each other so as to face at an angle to the opposed upper and lower implant surfaces, but are further angled towards the midline of the implant as shown in FIG. 37.

FIG. 40B shows trailing end 604' of implant 600', which is a bone ring, such as a femoral ring of cortical bone. Trailing end 604' has bone screw receiving holes 630a–630d for receiving bone screws 642 therein. Bone screw receiving holes 630a' and 630d' are oriented toward lower surface 608' for engaging a vertebral body above implant 600'. Opposed bone screw receiving openings 630b' and 630c' are oriented toward upper surface 606' for engaging a vertebral body below implant 600'. Accordingly, it is appreciated that as used herein the term "opposed" is not limited to being diametrically opposed, but includes opposite facing screw holes that are offset from one another. Preferably as described herein a lock or locks are provided to retain the screws when passing at least in part, and retained at least part through the openings.

Figure 41:
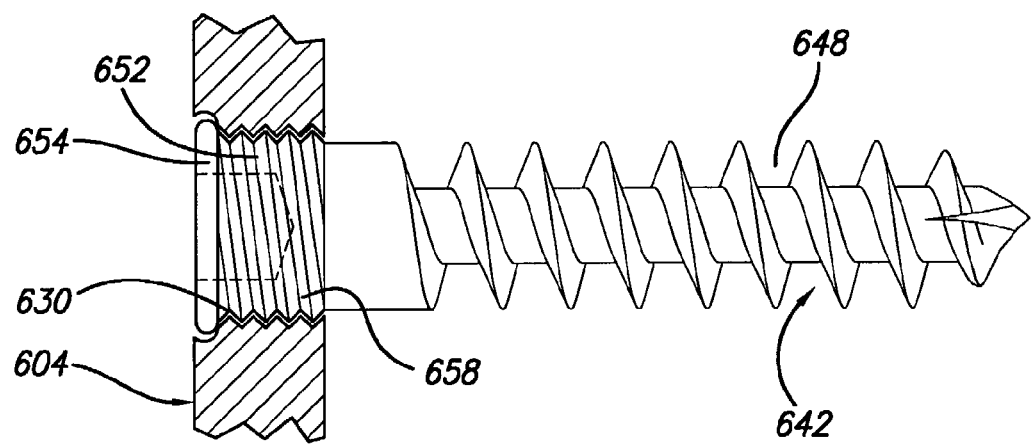
FIG. 41 is a detailed side elevation view in partial cross section of a portion of the rear of the sixth embodiment implant and the bone screw.
Figure 42:
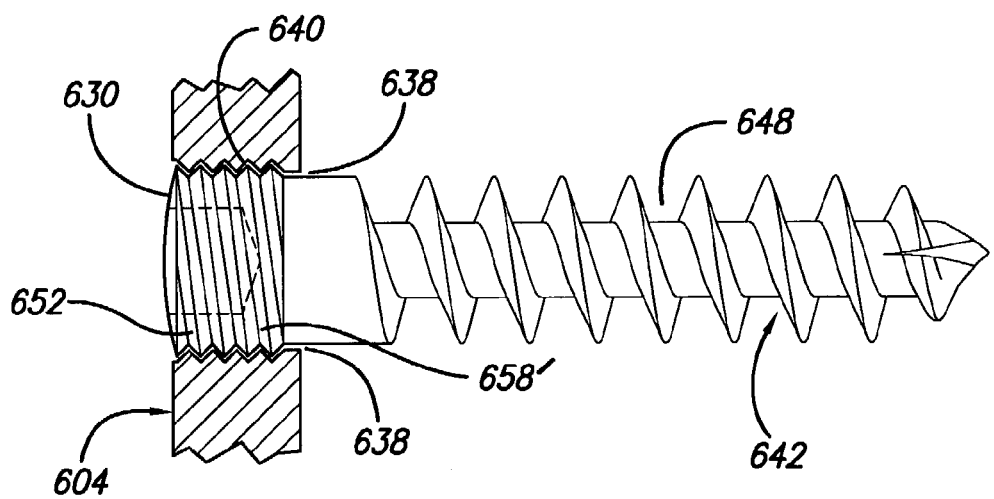
FIG. 42 is a detailed side elevation view in partial cross section of the rear wall of the sixth embodiment implant and an alternative screw.

As shown in FIGS. 41 and 42, holes 630 in a preferred embodiment have threaded walls 640. In a first example as shown in FIG. 41, bone screw 642 has a head portion 652 having a threaded portion 658 for threadably engaging the threaded wall 640 in hole 630 of implant trailing end 604. Screw head 652 also has an enlarged head portion 654 incapable of passing through the threaded portion of hole 630 and further allowing for bone screw 642 to be securely tightened down to and against the implant, thereby locking it to the implant.

FIG. 42 illustrates an alternative design for a self-locking screw as a variation to that shown in FIG. 41. Screw 642' has a hex drive 654 similar to screw 642. Also like screw 642, screw 642' has a threaded shaft 648 and a threaded head portion 658'. However, unlike screw 642, screw 642' does not have an additional enlarged head portion such as portion 654 of screw 642, but rather relies on flange portion 638 of opening 630 to stop the further progression of the screw head 652' through the implant and allow for head 652' to be securely tightened to the implant trailing end 604.

As a further alternative to both screws 642 and 642' being rigidly secured to implant 600 and resistant to any angular motion thereto, the trailing end of the implant includes a rotatable bearing having a threaded passageway therethrough and externally, at least in part, a curved profile allowing for the bearing to be trapped within rear wall 604 of the implant while still leaving it free to rotate within a complimentary socket formed therein. Because the screw threadably engages within the bearing, which is trapped within the rear wall of the implant it can be securely tightened to the bearing while yet still being free to move. In an alternative design, the bearing has slits and the screwhead, upon final tightening, expands the bearing so that it presses against the bearing retaining socket of the rear wall, locking the screw-bearing complex to the back of the implant to the extent desired. In a further variation of the 642 type screw the head may slightly flare outward from distal to proximal with expansion/compression slots therethrough allowing the head to be self locking within the threaded opening of the implant or a bearing as described above.

Figure 43:
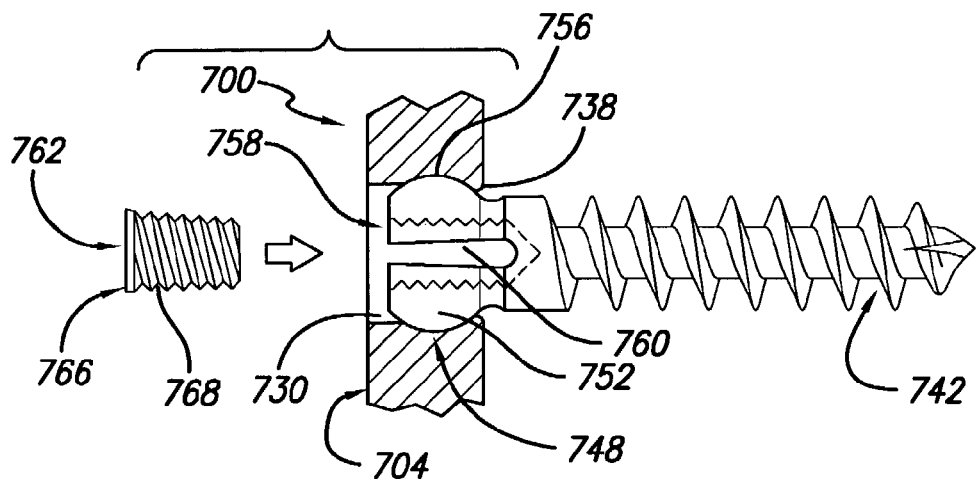
FIGS. 43, 44, and 45 are side elevation views in partial cross section showing a portion of the rear wall of one of the embodiments of the implants of the present invention and an alternative screw and lock mechanism.
Figure 44:
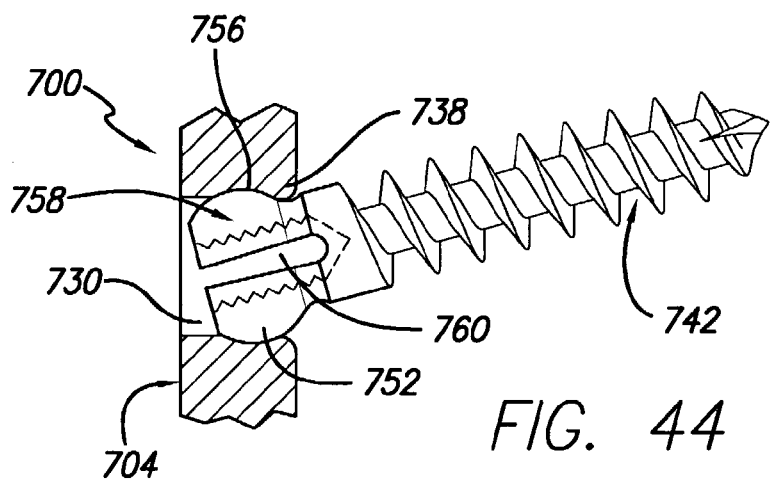
Figure 45:
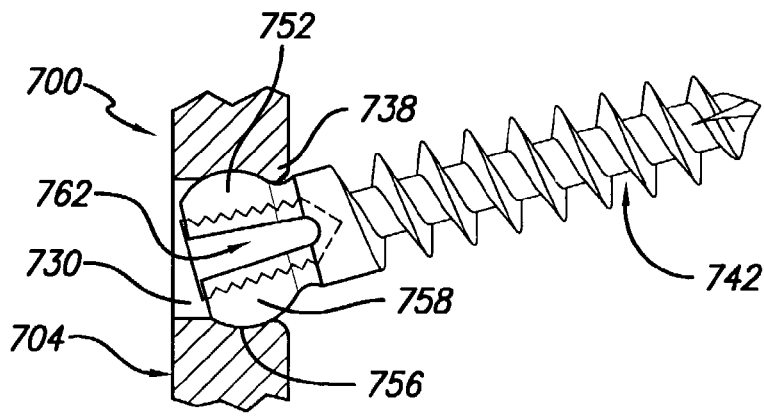

FIGS. 43 through 45 show an alternative embodiment of a locking screw mechanism which can be adapted for use with various of the other shown and/or described implant embodiments of the present invention. Trailing end 704 of an implant 700 has a hole 730 for accepting a bone screw 742. Bone screw 742 has a head portion 752 having at least a part about its perimeter a convex surface 756 having a maximum diameter. Bone screw receiving hole 730 has a circumferential concavity portion 748 for receiving convexity portion 756 of the bone screw head. Bone screw head 752 has internal threads 758 and a plurality of slots 760, preferably four. Slots 760 allow screw 742 to be driven with a cruciate type driver and allow for head 752 to sufficiently compress to be fully received within hole 730 of the implant. It can be appreciated from FIGS. 43 through 45 that screw 742 can be placed at an angle to the implant 700. Further, once the bone screw has been fully engaged into the adjacent vertebral body, the screw can be further rotated, allowing the vertebral body to be lagged to the implant, increasing the compressive load. Once a screw has been properly placed and tightened to the extent desired by the surgeon, a locking screw 762 having a head 766 and a threaded shaft 768 may be threaded into the threaded interior of the head 752 of bone screw 742. The implant screw locking system of FIGS. 43 through 45 can be manufactured such that while the locking screw 762 may be lockably tightened to the bone screw 742, and thus the backward migration of 742 from the implant prevented, the system can be designed so as to either allow for angular motion after the locking screw 762 is locked to the bone screw 742 or to prevent it. The function of the head in its ability to rotate and angulate within the implant is not dissimilar to the above described variation of the self locking screw and rounded bearing combination.

Figure 46A:
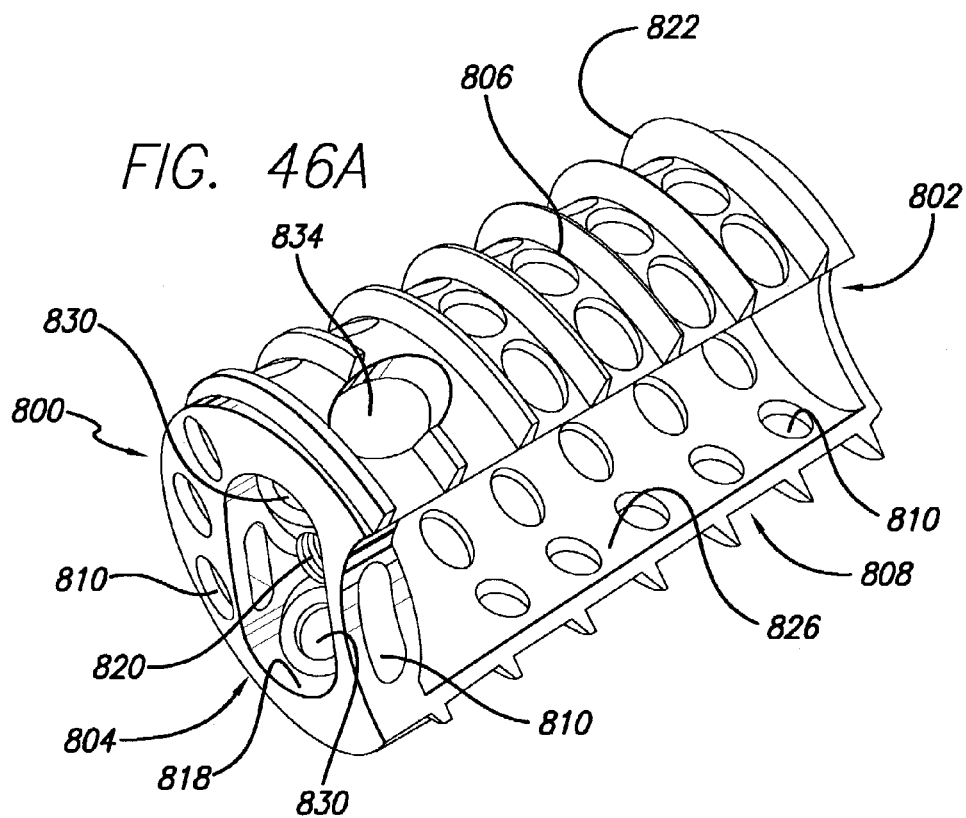
FIG. 46A is a side perspective side view of an eighth embodiment of an implant of the present invention.

FIGS. 46A through 53 show an eight and ninth embodiment of the present invention. Implants 800 and 900, which are shown in FIGS. 46A–46C can be used by themselves, or with a second of their kind, or as a complimentary pair as well shown in FIGS. 46D and 46F.

FIGS. 46A–53 show implants 800 and 900 and a series of steps useful for discussing a method of use of the present invention implants. Methods for inserting spinal implants are discussed in part in issued and pending patent applications to Michelson U.S. Pat. Nos. 5,593,409, 5,741,253, 5,484,437, Ser. Nos. 08/396,414, and 08/480,904, incorporated herein by reference. The disc space to be used is preferably, but not necessarily, distracted to optimal height and the vertebral bodies preferably, but not necessarily, properly aligned. A pair of overlapping bores, as best illustrated in FIG. 46D, are then formed across the disc space with a bone removal device, as shown in FIG. 46E. The bone removal device is preferably a drill having a diameter greater than the height of a distracted disc space such that arc-shaped portions of bone are removed from each of the vertebral bodies adjacent the disc space to be fused. The overlapping bores are generally oriented from anterior to posterior and preferably stop short of the spinal canal.

A bone removal device such as a drill or mill that may be conical can be utilized to complement the tapered configuration of the implant body. As shown in FIG. 46E, however, in a preferred method a generally cylindrical drill DR or end mill is utilized to create a generally cylindrical bore "B" for receiving the implants. When a pair of generally cylindrical overlapping bores, preferably but not necessarily, having a diameter generally corresponding to that of the root diameter of the implant proximate the leading end are formed as per FIG. 46D, the implants will come to be positioned such that the combined width of the implants at their leading ends will be less than the combined width of implants at their trailing end. That is, the implants will be angled in towards each other from anterior to posterior. This has the further benefit of swinging the junction of the lateral side walls and trailing ends further inward and away from escaping the anterior vertebral cortex, thereby avoiding protrusion of the lateral side wall to trailing end junctions and allowing for the installation of larger and longer implants than might otherwise be possible.

As has been taught by Michelson in the above identified applications and patents incorporated by reference herein, the disc space may be distracted in any number of ways and held distracted during the bore formation portion of the procedure. Some of the preferred ways include the use of long distractors, short distractors, and extended outer sleeves having distractor members for placement within the disc space and between the adjacent vertebral bodies as described by Michelson in the above described applications and patents incorporated by reference herein. Other distractors such as those which attach to the vertebral bodies as by pins or screws might also be useful for the present intended purpose.

While surgery may be performed through a single bore first, in a preferred embodiment both bores are created in overlapping fashion prior to the insertion of the first implant which in this example is implant 800. Implant 800 is affixed to an implant driver, which preferably engages the implant at trailing wall 804 by interdigitating with implant 800 and further binding to implant 800 by a thread such that it is possible both to rotate implant 800 in either direction and to push or pull simultaneously. While that may be achieved by having a driver which interdigitates with any of the openings into or through rear wall 804 and having a rotatable portion for threading into threaded opening 820 the present invention is not so limited and may include any driver useful for the intended purpose.

After implant 800 is fully seated with the medial side wall oriented immediately toward the disc space, a complementary implant 900 is inserted by allowing it to rotate within the maximum circumference of implant 800. Pre-tapping the bores formed across the disc space prior to the insertion of the implants does not deviate from the present teaching. In a preferred embodiment, pre-tapping is not required as certain preferred embodiments of the present implants are tapered from their trailing to their leading ends and the leading ends have particularly significant thread heights making their ability to thread themselves into the bone particularly effective.

Figure 46B:
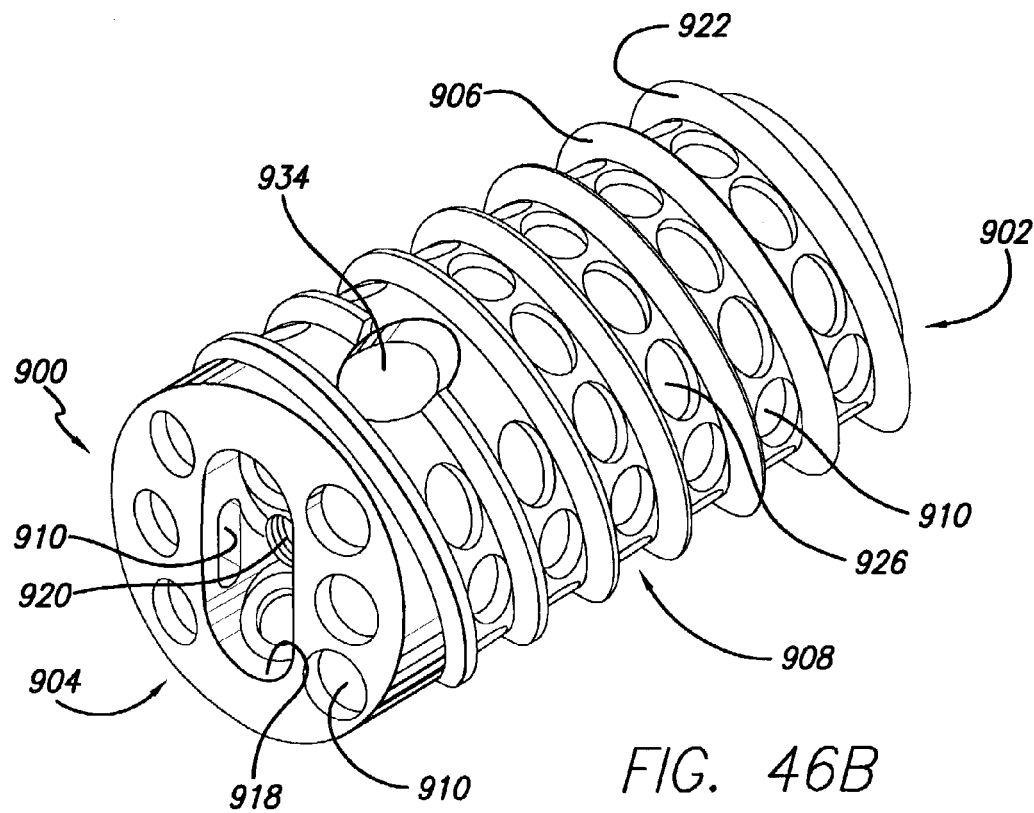
FIG. 46B is a side perspective view of a ninth embodiment of an implant of the present invention.
Figure 46C:
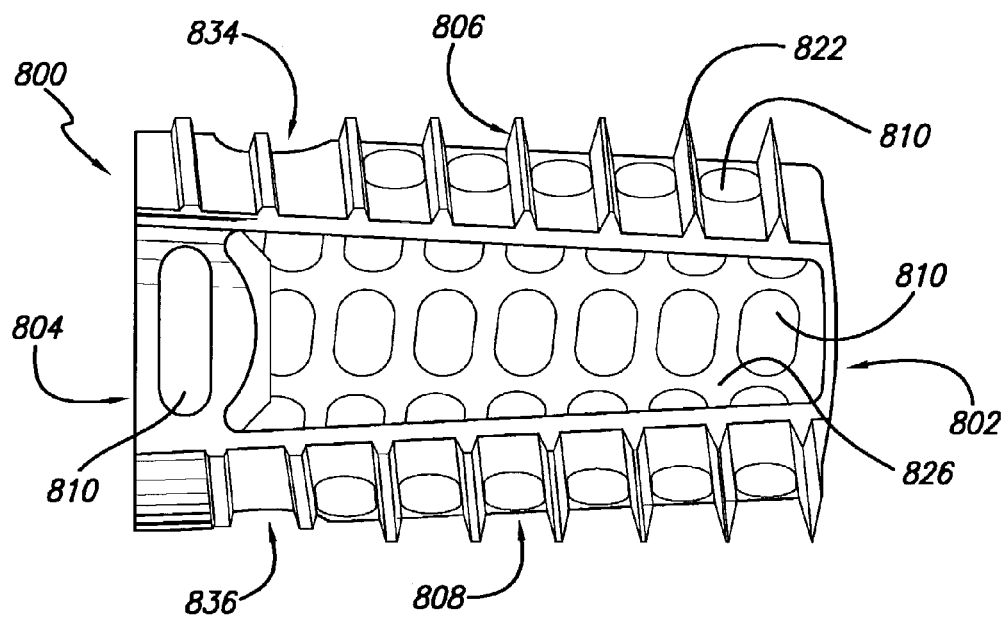
FIG. 46C is a side elevation view of the implant of FIG. 46A.
Figure 46D:
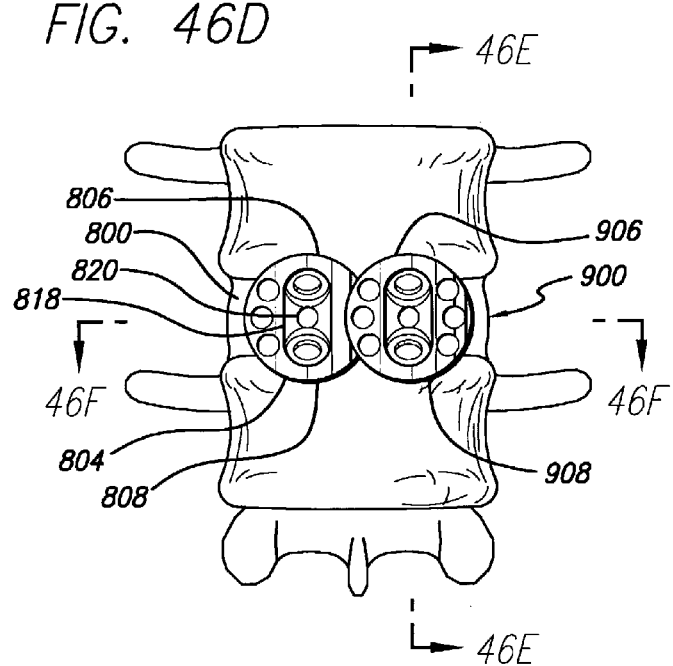
FIG. 46D is a trailing end view of the implants of FIGS. 46A and 46B, properly inserted within a spine.
Figure 46E:
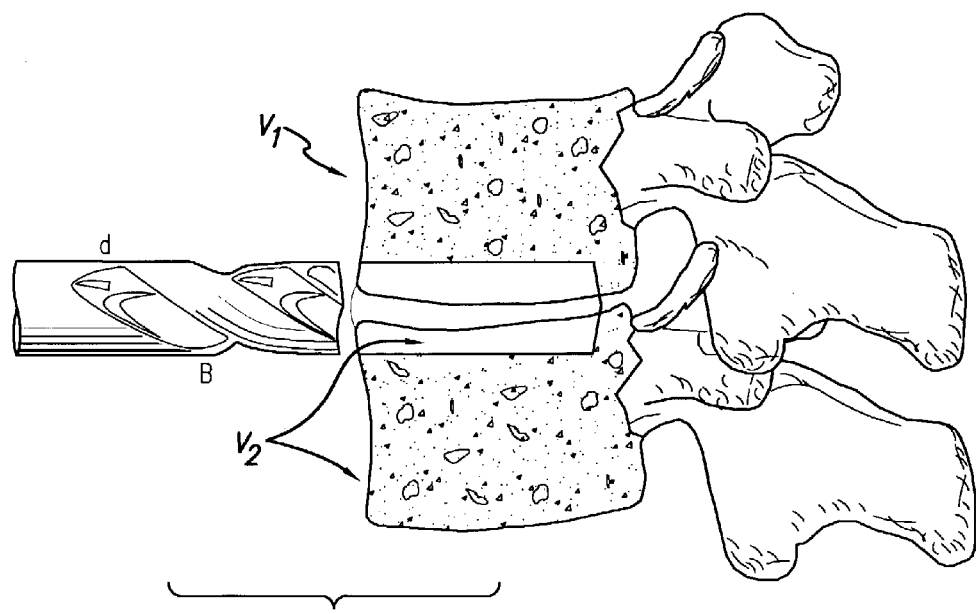
FIG. 46E is a side elevation view in partial cross section, showing the formation of a generally cylindrical bore across a disc space in a spine.
Figure 46F:
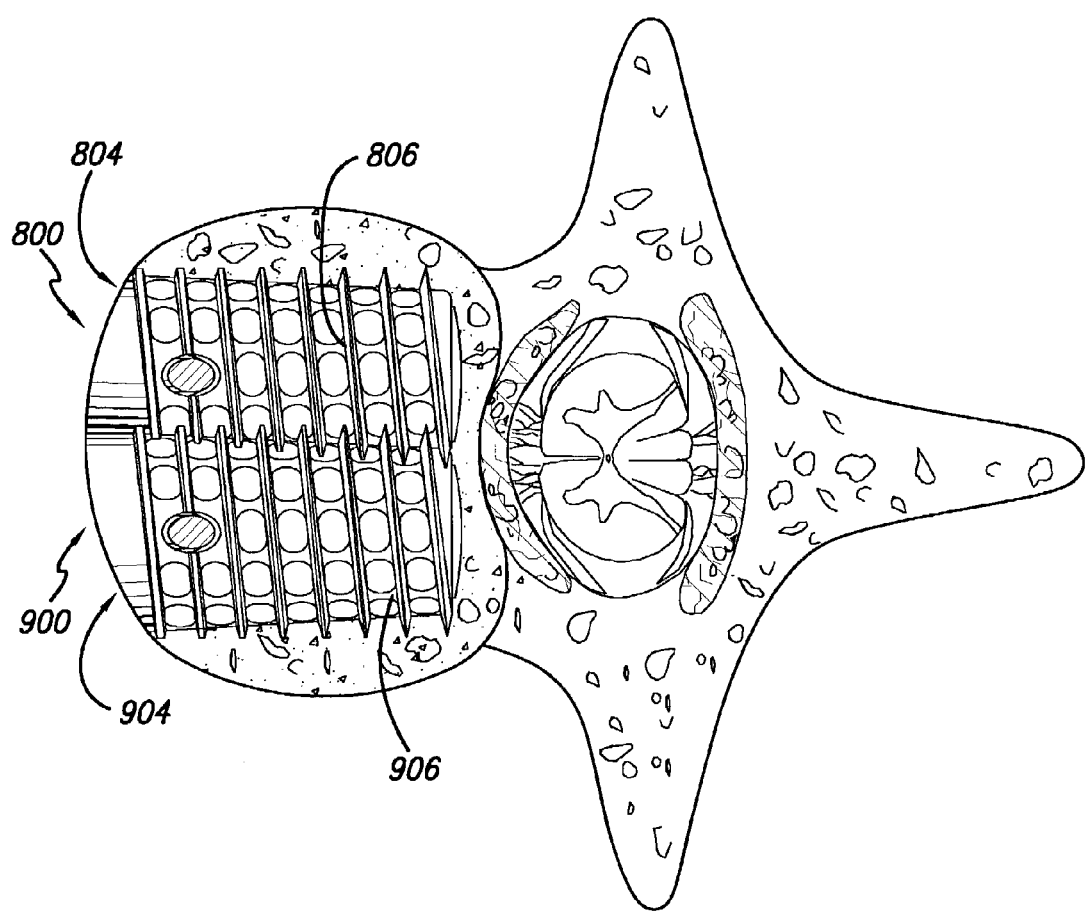
FIG. 46F is a top plan view along line 46F—46F of FIG. 46D.
Figure 50:
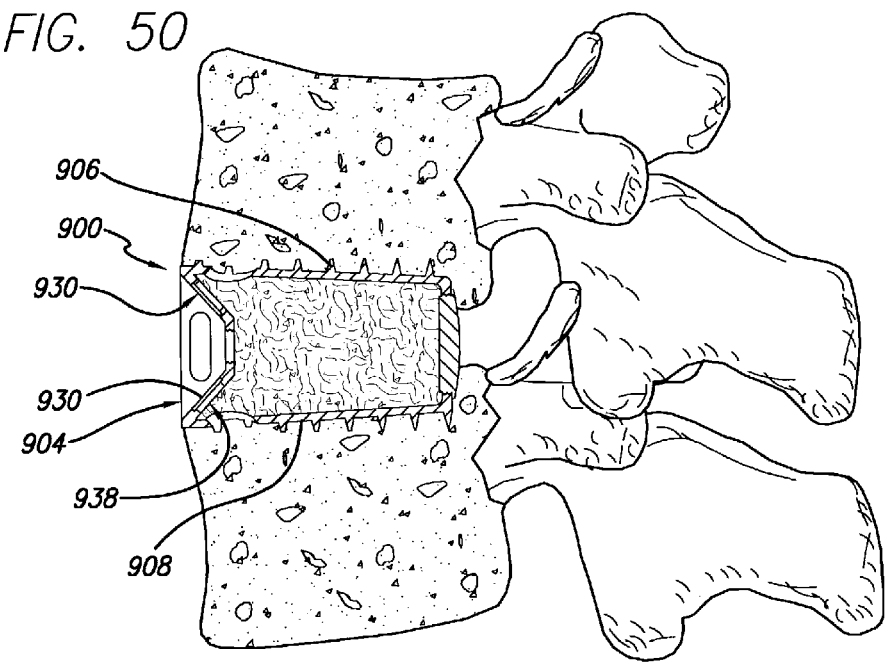
FIGS. 50, 51, 52, and 53 are side elevation views in partial cutaway illustrating the method of use of the driver of FIGS. 47A and 47B and the self-locking screw of FIG. 49 in relation to the ninth embodiment of the present invention properly inserted in a spine.
Figure 51:
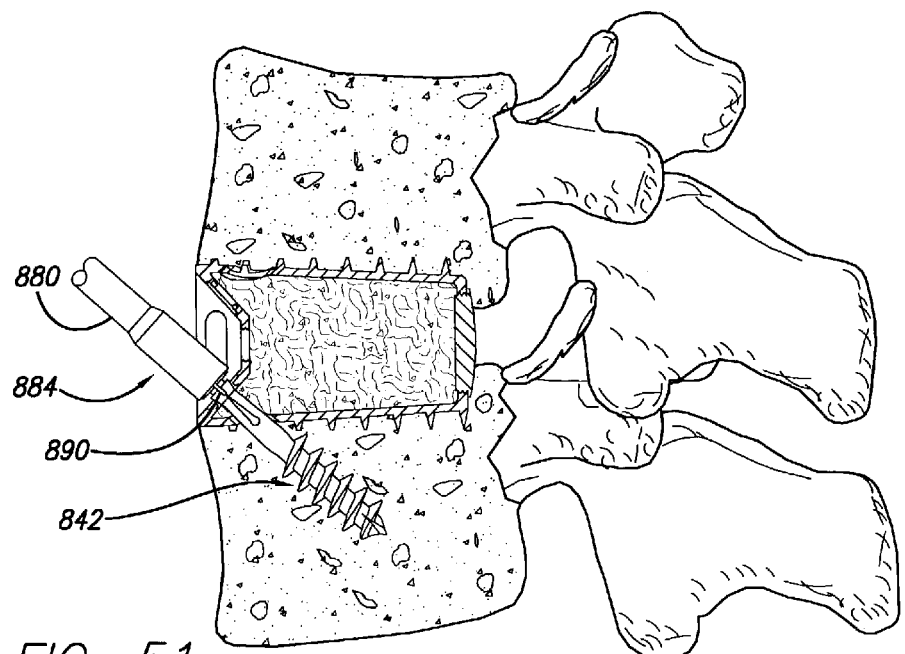
Figure 52:
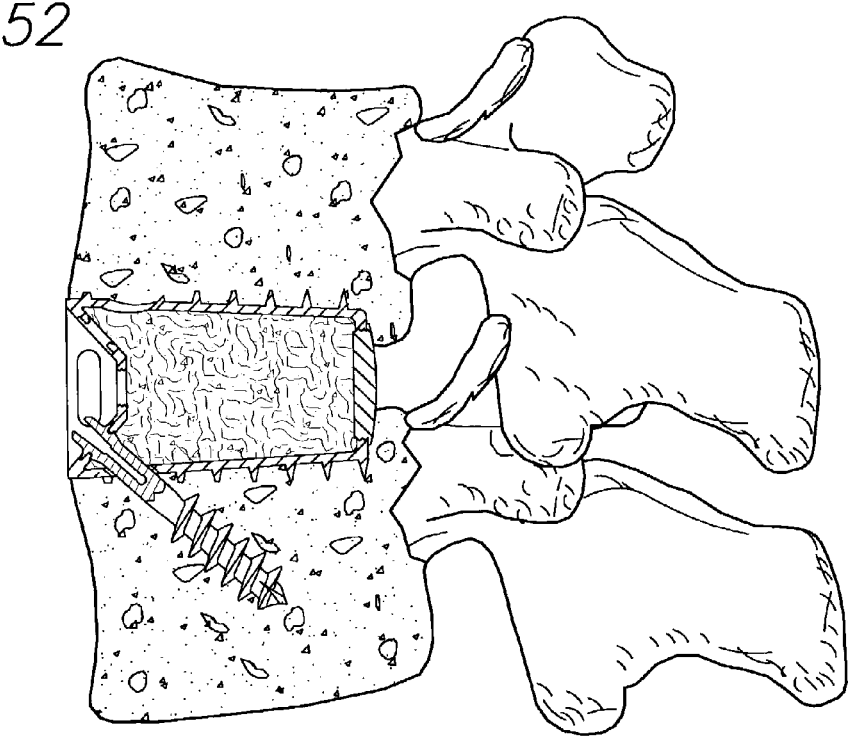
Figure 53:
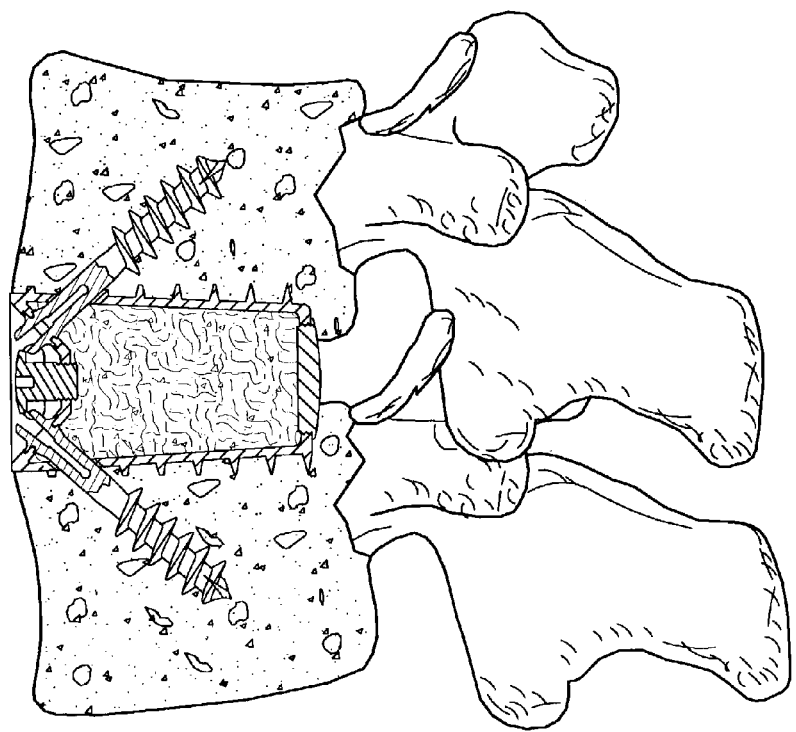

FIGS. 46A, 46B and 46D, show openings at the trailing end of the implant for receiving opposed screws that may be oriented from the implant into each of the adjacent vertebral bodies. These screws enter the implant through the trailing end and the threaded shafts of the screws pass through openings in the opposite upper and lower vertebral body engaging surfaces of the implants. Shown in FIGS. 50–53 is a cut away through implant 900 of FIG. 46B. This is a cross section through the mid-longitudinal axis of implant 900 and the adjacent vertebral bodies. FIGS. 47A and 47B show a screw driver 880 and FIG. 51 shows driver 880 driving a bone screw 842 through bone screw receiving hole 930 and out 842 through lower vertebrae engaging surface 908 into adjacent vertebral body $V_2$.

The present invention includes the use of any bone screws for this described purpose. In preferred embodiments, structure is provided to block the bone screws from disengaging from the implant or backing out. The screws may be rigidly locked to the implant or may be prevented from backing out in a manner that still allows for some relative motion between the screws and the implant. The latter may be beneficial for anticipating and allowing for some settling of the vertebral bodies towards the disc space. In use, as shown in FIG. 51, the driver 880 is assembled to the screw 842 thereby compressing the head portion of the screw. The screw is then introduced through the trailing end of the implant and directed into the body of one of the adjacent vertebrae passing out of an opening adapted for that purpose in one of the opposite vertebrae engaging surfaces of the implant. The head of the screw 842 is too large to pass through the opening in the implant, and yet is free to spin against the implant itself making it possible to lag the screw, or that is to draw the body of the vertebra to the implant and to generate compressive load between the implant and the vertebral body.

FIGS. 46A and 46C show a preferred embodiment of implant 800. The lateral side wall and medial side wall have a distance therebetween defining an implant width transverse to the implant height. The width of implant 800 is less than its height along at least a portion of its length. The medial side wall is preferably configured to be positioned in close proximity to at least implant 900 such that the combined width of implants 800, 900 is less than the combined height of those implants.

Implant 800 is similar to implant 900, but differs from implant 900 in that while the lateral sides of implants 800 and 900, respectively, are the same and in this example convex, the medial side of implant 800 has been relieved so as to allow for the convex medial side of implant 900 to protrude therein. Alternatively, the medial side of implant 800 can be relieved, in part absent, and/or concave.

Implant 800 also has at the medial side a convexity as shown by the contour of trailing support wall 804. In a preferred embodiment, leading support wall 802 may similarly be concave. And further a portion of the medial side wall is absent so as to allow for the protrusion of implant 900 therein.

As shown in FIG. 46B, thread 922 of implant 900 may have a generally constant outer diameter. Inasmuch as the body of implant 900 is generally conical such that it tapers from the larger trailing end 904 to the smaller leading end 902, the height of thread 922 relative to the body increases from trailing end 904 to leading end 902. Thus, while the outer diameter of the threads remains generally constant, the height of the thread increases from trailing end 904 to leading end 902. This is similarly true for implant 800.

In a preferred embodiment of implants 800, 900 the start of the external thread about the perimeter of the implant is precisely indexed such that if the surgeon knows the depth of the bore created, he may select an implant of the desired length being less than or equal to the depth of the bore created and by starting the insertion of the implant in a preferred rotational alignment such as the desired final rotational alignment the implant when threaded in fully will come to rest such that trailing end 804, 904 will be correctly rotationally aligned so that the screw receiving holes 834, 836, 934, 936 will be oriented correctly towards the adjacent vertebral bodies while the profile of trailing ends 804, 904 will correspond to the contour of the anterior vertebral body.

By way of example, for a bore measured to receive a 30 millimeter maximum length implant having a pitch of three millimeters as an example, the start of the thread at the implant leading end could be indexed such that the implant could be introduced rotationally oriented exactly as desired for the final positioning. Then, by making ten complete revolutions of three millimeters each the implant would assuredly come to rest with trailing wall 804 appropriately oriented and either be flush with the anterior vertebral cortices, or minimally counter-sunk to exactly the extent to which the surgeon caused the implant to enter the bore prior to initiating rotation. As previously mentioned, trailing end 804 of implant 800 could be rotationally asymmetrical, but nevertheless be symmetrical from side-to-side, such that each of the sides of the implant would be less protuberant posteriorly than a point along the mid-longitudinal axis such that the implant could be correctly inserted in increments of less than or equal to 180 degrees of rotation.

As shown in FIGS. 48 and 49, screw 842 has a threaded shaft 848 having a leading end 844, a tip 846, and an opposite trailing end 852. Shaft 848 has a thread form for engaging bone. Trailing end 852 has a screw head having an enlarged portion 856 having a diameter greater than the outer diameter of the threaded portion of shaft 848. The screw head has a cruciate recess 861 for receiving the end 890 of screw driver 880.

FIG. 46B shows a front view of an embodiment of the present invention with implants 800, 900 properly implanted across the disc space between adjacent vertebral bodies $V_1$ and $V_2$. Openings 820, 920 also are adapted to receive a screw device to link the implant to other implants, to a staple, or to receive a locking screw to lock bone engaging screws to the implant as disclosed in Michelson U.S. patent application Ser. No. 08/926,334 incorporated herein by reference. As shown in the preferred embodiment of the present invention, trailing ends 804 and 904 of implants 800 and 900, respectively, preferably are rotationally asymmetrical about the longitudinal axes of the implants such that the designated medial side of each of the implants has a length greater than the lateral sides of the same implants. Trailing ends 804, 904 preferably are structured to have a lesser length along their lateral sides than through the mid-longitudinal axis and are preferably contoured so as to sit on the anterior rims of the vertebral bodies without protruding dangerously therefrom as set forth in pending Michelson application Ser. No. 09/263,266 incorporated herein by reference. In another embodiment of the present invention, the trailing ends of the implants can have a maximum length along the mid-longitudinal axis greater than the length along either of the medial and lateral sidewalls so that the bone screw receiving holes can be oriented towards the adjacent vertebral bodies in half rotation increments rather than requiring a full rotation. While for implant 900 this would require no other modification than as described for the trailing end, in regard to implant 800 each of the lateral and medial side walls would have to be relieved to allow for the receipt of the perimeter of implant 900 within the maximum perimeter of implant 800.

In each of the examples of the present invention as offered, it is understood that the invention is limited to screws that are appropriate for their intended purpose and thus related to the overall size of the implant as it relates to the region of the spine for which it is configured for implantation.

Specifically, the screws of the present invention have the following preferred size. When for use in the lumbar spine, the screws have at least partially threaded shafts having outer diameters (major diameter) not less than 4.8 mm and not greater than 10 mm with 6 mm to 8 mm generally preferred. A preferred root diameter is at least 1.5 mm less than the outer diameter and most preferably 2.5 mm to 5 mm. When the screw is used from anterior to posterior, a length of from 10 mm to 40 mm is preferred with 20 mm to 30 mm being more preferred. When the screw is used in a lateral approach, a length of from 10–50 mm is preferred with 25–35 mm being more preferred.

The screws preferably have head portions having an outside dimension generally equal to or greater than the outer diameter of the thread of the threaded shaft. An exception is where the head has an outwardly facing machine thread and the shaft has a cancellous thread with the turns or pitch of the thread being spaced apart to exceed the wall thickness of that portion of the implant adapted to retain the screw head.

Further, the screws preferably have pointed leading ends and are self tapping with cutting flutes and have an interrupted thread at their leading end. The screws preferably have a smooth shaft portion proximally near the head. All screws preferably have at their trailing ends adapted for cooperatively engaging a screw driver.

Screws used in the cervical spine vary from screws used in the lumbar spine in that a preferred major diameter is 3.5–5.5 mm with 4.0 mm to 5.0 mm being more preferred. A preferred length is from 8–20 mm with 12–16 mm being more preferred.

Preferred screws for use in the thoracic spine vary from screws used in the lumbar and cervical spine in that a preferred thread has an outer diameter from 4–8 mm with 5–7 mm being more preferred. The screws having a length of from 10 mm to 30 mm with a length of approximately 20 mm plus or minus 5 mm being more preferred.

It is believed that the operation and construction of the present invention will be apparent from the foregoing description and, while the invention shown and described herein has been characterized as particular embodiments, changes and modifications may be made therein without departing from the spirit and scope of the invention, which is limited only by the scope of the claims.

What is claimed is:

1. An apparatus comprising:
an interbody spinal fusion implant for surgical implantation at least in part within a disc space between two adjacent vertebral bodies in a segment of a human spine, said implant comprising an interior, a leading end for entry into the spine, a trailing end opposite said leading end, and a length therebetween, and upper and lower portions for contacting each of the adjacent vertebral bodies when positioned therein, said upper and lower portions having a maximum height therebetween, each of said upper and lower portions having at least one opening adapted to communicate with one of the adjacent vertebral bodies, said openings in said upper and lower portions being in communication with one another and adapted to permit for the growth of bone from adjacent vertebral body to adjacent vertebral body through said implant, said trailing end having an interior and an outermost exterior surface opposite said leading end, said implant including at least two vertebral body penetrating member receiving holes passing through said interior of said trailing end, through said interior of said implant, and through each of said upper and lower portions proximate said trailing end, said trailing end having at least one aperture in communication with at least one of said vertebral body penetrating member receiving holes in said upper and lower portions;
vertebral body penetrating members adapted for placement through said at least one aperture in said trailing end, through at least a portion of said interior of said trailing end, and through said holes in said upper and lower portions and into each of the adjacent vertebral bodies adjacent the disc space to be fused and into which said implant is adapted to be positioned; and
a cap adapted to be coupled to said trailing end of said implant to prevent movement of said vertebral body penetrating members in a direction opposite to the direction of insertion of said vertebral body penetrating members into said aperture in said trailing end of said implant, said cap having a maximum dimension being less than the maximum height between said upper and lower portions of said implant.

2. The apparatus of claim 1, wherein said implant further comprises a hollow interior for holding bone growth promoting material, said hollow interior being in communication with said at least one opening in each of said upper and lower portions.

3. The apparatus of claim 1, wherein said vertebral body penetrating member receiving holes are opposed and divergently angled to one another.

4. The apparatus of claim 1, wherein said implant has a mid-longitudinal axis, said vertebral body penetrating member receiving holes being angled between 25 and 75 degrees from said mid-longitudinal axis of said implant.

5. The apparatus of claim 1 wherein said vertebral body penetrating member receiving holes are opposed and divergently angled and extend from said trailing end and through said upper and lower portions.

6. The apparatus of claim 5, wherein said vertebral body penetrating member receiving holes extending from said trailing end are configured so as to be adapted to be oriented towards the adjacent vertebral bodies in half rotation increments of said implant.

7. The apparatus of claim 1, wherein at least a portion of said vertebral body penetrating members is adapted to pass from said interior of said implant through said vertebral body penetrating member receiving holes and into the adjacent vertebral body to anchor said implant to the adjacent vertebral body.

8. The apparatus of claim 1, wherein said vertebral body penetrating members have a sharp distal end.

9. The apparatus of claim 1, wherein said vertebral body penetrating members have a distal end and a head opposite said distal end, said head being adapted to engage a driving instrument.

10. The apparatus of claim 1, wherein said vertebral body penetrating members are at least in part made of a resorbable material.

11. The apparatus of claim 1, wherein said vertebral body penetrating members comprise a metal suitable for human implantation.

12. The apparatus of claim 1, wherein said trailing end of said implant is configured to cooperatively engage an implant driver.

13. The apparatus of claim 1, wherein said cap has a bearing surface for bearing against a portion of at least one of said vertebral body penetrating members.

14. The apparatus of claim 1, wherein said cap comprises a threaded member.

15. The apparatus of claim 1, wherein said cap covers at least a portion of at least one of said at least one apertures in said trailing end of said implant and said vertebral body penetrating member receiving holes.

16. The apparatus of claim 1, wherein said upper and lower portions are parallel to one another.

17. The apparatus of claim 1, wherein said upper and lower portions are convergent to one another.

18. The apparatus of claim 1, wherein said upper and lower portions are generally planar surfaces.

19. The apparatus of claim 1, wherein said upper and lower portions are opposed arcuate portions.

20. The apparatus of claim 19, wherein said opposed arcuate portions form at least a portion of a cylinder along the length of said implant.

21. The apparatus of claim 1, wherein each of said tipper and lower portions have at least one bone engaging projection thereon.

22. The apparatus of claim 21, wherein said projection is at least one of a fin, a ridge, and a thread.

23. The apparatus of claim 2, wherein at least one of said leading and trailing ends is open to allow access to said hollow interior.

24. The apparatus of claim 1, wherein said implant comprises an artificial material other than bone.

25. The apparatus of claim 1, wherein said implant is made of an artificial material that is stronger than bone.

26. The apparatus of claim 1, wherein said implant is made of an artificial material that is harder than bone.

27. The apparatus of claim 1, wherein said implant comprises bone.

28. The apparatus of claim 1, wherein said implant comprises bone growth promoting material.

29. The apparatus of claim 28, wherein said bone promoting material is compressive loaded into said implant.

30. The apparatus of claim 28, wherein said bone growth promoting material is selected from one of bone morphogenetic protein, hydroxyapatite, and genes coding for the production of bone.

31. The apparatus of claim 1, wherein said implant is treated with a bone growth promoting substance.

32. The apparatus of claim 1, wherein said implant is a source of osteogenesis.

33. The apparatus of claim 1, wherein said implant is at least in part bioabsorbable.

34. The apparatus of claim 1, wherein said implant comprises a plastic material.

35. The apparatus of claim 1, wherein said implant comprises a ceramic material.

36. The apparatus of claim 1, wherein said implant is formed of a porous material.

37. The apparatus of claim 1, wherein said implant is formed of a material that intrinsically participates in the growth of bone from adjacent vertebral body to adjacent vertebral body through said implant.

38. The apparatus of claim 1, in combination with a chemical substance to inhibit scar formation.

39. The apparatus of claim 1, in combination with a fusion promoting substance.

40. The apparatus of claim 39, wherein said fusion promoting substance includes at least one of bone, bone morphogenetic protein, hydroxyapatite, and genetic materials coding for the production of bone.

41. The apparatus of claim 1, in combination with an orthopedic device for use in spinal surgery.

42. The apparatus of claim 41, wherein said orthopedic device is a bone removal device for preparing a space between and at least in part into the adjacent vertebral bodies.

43. The apparatus of claim 42, wherein said bone removal device is one of a drill and a mill.

44. The apparatus of claim 41, wherein said orthopedic device is an implant driver for inserting said spinal implant.

45. The apparatus of claim 41, wherein said orthopedic device is a distractor for distracting the disc space between the adjacent vertebral bodies.

46. The apparatus of claim 41, wherein said orthopedic device is a sleeve for providing protected access to the disc space between the adjacent vertebral bodies.

47. The apparatus of claim 1, wherein said cap has a central longitudinal axis, a maximum dimension transverse to the central longitudinal axis, and an outer perimeter defined by the maximum transverse dimension, said outer perimeter being threaded.

48. The apparatus of claim 1, wherein said cap is threaded, said cap having a central longitudinal axis and a thread diameter transverse to the central longitudinal axis, each of said vertebral body penetrating members having a longitudinal axis and a thread diameter transverse to the longitudinal axis, the thread diameter of said cap being greater than the thread diameter of at least one of said vertebral body penetrating members.

49. The apparatus of claim 1, further comprising at least a second cap adapted to be coupled to said trailing end of said implant to prevent movement of at least one of said vertebral body penetrating members in a direction opposite to the direction of insertion of said at least one of said at least one of said vertebral body penetrating members into said aperture in said trailing end of said implant.

* * * * *

UNITED STATES PATENT AND TRADEMARK OFFICE
CERTIFICATE OF CORRECTION

| | | |
|---|---|---|
| PATENT NO. | : 7,033,394 B2 | Page 1 of 1 |
| APPLICATION NO. | : 10/444216 | |
| DATED | : April 25, 2006 | |
| INVENTOR(S) | : Gary K. Michelson | |

It is certified that error appears in the above-identified patent and that said Letters Patent is hereby corrected as shown below:

Column 20, line 16:
Change "claim 1" to -- claim 1, --.

Column 21, line 1:
Change "tipper" to -- upper --.

Signed and Sealed this

Eleventh Day of July, 2006

JON W. DUDAS
*Director of the United States Patent and Trademark Office*